US007612039B2

(12) United States Patent
Khalili

(10) Patent No.: US 7,612,039 B2

(45) Date of Patent: Nov. 3, 2009

(54) METHOD OF CELL GROWTH INHIBITION WITH AGNOPROTEIN

(75) Inventor: Kamel Khalili, Merion, PA (US)

(73) Assignee: Temple University - Of The Commonwealth System of Higher Education, Philadelphia, PA (US)

(*) Notice: Subject to any disclaimer, the term of this patent is extended or adjusted under 35 U.S.C. 154(b) by 221 days.

(21) Appl. No.: 10/517,710

(22) PCT Filed: Jun. 11, 2003

(86) PCT No.: PCT/US03/18519

§ 371 (c)(1),
(2), (4) Date: Jul. 27, 2005

(87) PCT Pub. No.: WO03/106626

PCT Pub. Date: Dec. 24, 2003

(65) Prior Publication Data

US 2006/0052296 A1 Mar. 9, 2006

Related U.S. Application Data

(60) Provisional application No. 60/388,019, filed on Jun. 12, 2002.

(51) Int. Cl.
*A61K 38/00* (2006.01)
*C07K 5/00* (2006.01)

(52) U.S. Cl. ........................................ 514/12; 530/324

(58) Field of Classification Search ....................... None
See application file for complete search history.

(56) References Cited

U.S. PATENT DOCUMENTS

| | | | | |
|---|---|---|---|---|
| 5,643,567 | A | 7/1997 | Hung et al. | 424/93.2 |
| 5,801,029 | A | 9/1998 | McCormick | 435/172.3 |
| 5,814,315 | A | 9/1998 | Hung et al. | 424/93.2 |
| 6,197,754 | B1 | 3/2001 | Hung et al. | 514/44 |
| 6,296,845 | B1 | 10/2001 | Sampson-Johannes et al. | 424/93.2 |
| 2001/0006633 | A1 | 7/2001 | Kirn | 424/93.6 |
| 2001/0048920 | A1 | 12/2001 | Lee et al. | 424/93.21 |

OTHER PUBLICATIONS

Skolnick et al. (Trends in Biotech., 18(1):34-39, 2000).*
Freshney (Culture of Animal Cells, A Manual of Basic Technique, Alan R. Liss, Inc., 1983, New York, p4).*
Dermer (Bio/Technology, 1994, 12:320).*
Gura (Science, 1997, 278:1041-1042).*
Jain (Sci. Am., 1994, 271:58-65).*
Verma et al. (Nature 1997, 389: 239-242).*
Amalfitano et al. (Current Gene Therapy 2002, 2: 111-133).*
Department of Health and Human Services has released a memorandum dated Jan. 14, 2003.*
Pandha et al. (Current Opinion in Investigational Drugs 2000; 1 (1): 122-134).*
Jay et al nature vol. 291 p. 346 (1981).*
Zhao et al., "Effect of $As_2O_3$ on cell cycle progression and cyclins D1 and B1 expression in two glioblastoma cell lines differing in p53 status," *Int'l J. Oncol.* 21: 49-55 (2002).
Yoshida et al., "In vitro inhibition of cell proliferation, viability, and invasiveness in U87MG human glioblastoma cells by estramustine phosphate," *Neurosurgery* 39: 360-66 (1996).
Richard J. Frisque et al., "Human Polyomavirus JC Virus Genome", *Journal of Virology*, vol. 51, No. 2, pp. 458-469 (1984).
DeValle L et al. (Feb. 11, 2002), "Expression of Human Neurotropic Polyomavirus JCV Late Gene Product Agnoprotein in Human Medullablastoma," *J. Nat. Cancer Inst.* 94(4).
Cubitt CL et al. (2001), "Predicted Amino Acid Sequences for 100 JCV Strains," *J Neurovirol.*, 7(4): 339-344.
Jobes DV et al. (1999), "A Novel JC Virus Variant Found in the Highlands of Papua New Guinea Has a 21-Base Pair Deletion in the Agnoprotein Gene," *J. Hum. Virol.* 2(6): 350-358.
Safak M et al. (2001), "Interaction of JC Virus Agno Protein with T Antigen Modulates Transcription and Replication of the Viral Genome in Glial Cells," *J. Virol.* 75(3): 1476-1486.
Stacy T et al. (1989), "Simian Virus 40 Host Range/Helper Function Mutations Cause Multiple Defects in Viral Late Gene Expression," *J. Virol.* 63(12): 5208-5215.
Khalili K et al. (1988), "Carboxyl-terminal mutants of the large tumor antigen of simian virus 40: A role for the early protein late in the lytic cycle," *Proc. Natl. Acad. Sci. USA* 85: 354-358.
Resnick J and Shenk T (1986), "Simian Virus 40 Agnoprotein Facilitates Normal Nuclear Location of the Major Capsid Polypeptide and Cell-to-Cell Spread of Virus," *J. Virol.* 60(3): 1098-1106.
Carswell S and Alwine J, "Simian Virus 40 Agnoprotein Facilitates Perinuclear-Nuclear Localization of VP1, the Major Capsid Protein," *J. Virol.* 60(3): 1055-1061, 1986.
Hay N and Aloni Y (1985), "Attenuation of Late Simian Virus 40 mRNA Synthesis Is Enhance by the Agnoprotein and Is Temporally Regulated in Isolated Nuclear Systems," *Mol. and Cell. Biol.*5(6): 1327-1334.
Nomura S et al (1983), "Subcellular Localization of the Simian Virus 40 Agnoprotein," *J. Virol.* 45(1): 428-433.
Alwine JC (1982), "Evidence for Simian Virus 40 Late Transcriptional Control: Mixed Infections of Wild-Type Simian Virus 40 and a Late Leader Deletion Mutant Exhibit *trans* Effects on Late Viral RNA Synthesis," *J. Virol.* 42(3): 798-803.
Hay N et al. (1982), "Attenuation in the Control of SV40 Gene Expression," *Cell.* 29: 183-193.

* cited by examiner

*Primary Examiner*—Sheela J Huff
(74) *Attorney, Agent, or Firm*—Daniel A. Monaco; Drinker Biddle & Reath LLP

(57) ABSTRACT

The growth of normal and abnormally proliferating cells can be inhibited by the introduction of agnoprotein, or biologically active fragments or derivatives of agnoprotein, into the cell in the absence of any other polyoma virus protein or viral replication.

20 Claims, 10 Drawing Sheets preimmune anti-Agnoprotein

METHOD OF CELL GROWTH INHIBITION WITH AGNOPROTEIN

REFERENCE TO GOVERNMENT GRANT

The invention described herein was supported in part by NIDN/NIH grant nos. P01 NS30916 and P01 NS36466. The U.S. government has certain rights in this invention.

FIELD OF THE INVENTION

This invention relates to methods of inhibiting cell growth with polyoma virus agnoproteins, especially with agnoprotein from the human neurotropic polyoma virus JCV.

BACKGROUND OF THE INVENTION

The polyoma viruses (Polyomaviridae) are DNA viruses which infect a variety of species, including man. There are two polyoma viruses that cause disease in humans; BK virus (isolated from an immunosuppressed kidney transplant patient) and the human neurotropic polyomavirus JCV. Other polyoma viruses include the simian polyoma virus SV40, and the murine and avian polyoma viruses.

JCV is an established etiologic agent of progressive multifocal leukoencephalopathy, a fatal demyelinating disease of humans. Alwine J C (1982), *J. Virol.* 42, 798-803. Recent studies point to the association of JCV with several human cancers, including tumors of neural origin. See, e.g., Del Valle L et al., (2001a) *Cancer Res* 61: 4287-4293; Caldarelli-Stefano R et al., (2000) *Human Pathol.* 31: 394-395; and Khalili K et al. (1999), *Lancet* 353: 1152-1153.

As with other polyomaviruses, the genome of JCV is comprised of a double-stranded circular DNA that contains three functional regions. These functional regions are the early and late coding genomes, and the non-coding regulatory sequence. Frisque R J et al. (1984), *J. Virol.* 51: 458-469. The early genome is responsible for expression of the viral regulatory protein T-antigen. The late genome is expressed after DNA replication and results in the accumulation of the capsid proteins VP1, VP2, and VP3. In addition, the leader sequences of the late genome transcripts encompass an open reading frame encoding the agnoprotein.

During the 1980's, several laboratories studied polyomavirus agnoprotein. In particular the biological function of agnoprotein in SV40-infected monkey kidney cells was investigated. See, e.g., Alwine J C (1982) supra and Khalili K (1988), *Proc. Natl Acad. Sci. USA* 85: 354-358. These studies show that SV40 agnoprotein is important for the late events of the viral lytic cycle. In more recent studies, JCV agnoprotein was shown to interact with early T-antigen. See, e.g., Safak M et al. (2001), *J. Virol.* 75: 1476-1486. These studies suggest that T-antigen activity in viral gene transcription and DNA replication may be dictated, at least in part, by the interaction of T-antigen with agnoprotein. Thus, agnoprotein appears to have an integral function in polyoma viral replication.

As mentioned above, JCV infection has been linked to various tumors of central nervous system (CNS) origin, including medullablastoma, glioblastoma, and others. Del Valle L et al., (2001a), supra; Khalili K (1999), supra. Examination of T-antigen expression in the CNS tumor tissue revealed that not all tumor cells express T-antigen. Evaluation of these tumors for other viral proteins showed a substantial level of agnoprotein in tumors containing the JCV genome. DeValle L et al. (2002), *J. Nat. Cancer Inst.* 94(4): 267-273.

The importance of agnogene expression in brain tumor cells is unknown. One hypothesis holds that interactions of T-antigen and agnoprotein with each other, and with endogenous cellular proteins, may modulate the growth rate of tumor cells. Nevertheless, it appears from the studies discussed above that JCV agnoprotein is involved in the development and growth of some CNS neoplasms.

SUMMARY OF THE INVENTION

Surprisingly, it has now been found that polyoma virus agnoproteins inhibit the growth of both normal and abnormally proliferating cells in the absence of other polyoma viral proteins.

The invention thus provides a method of inhibiting cell growth comprising introducing into a cell an effective amount of one or more agnoproteins, or one or more biologically active fragments or derivatives of agnoprotein, such that growth of the cell is inhibited.

The invention also provides a method of treating a subject having a cancer or a non-cancerous proliferative disorder, comprising administering to the subject an effective amount of one or more agnoproteins, or one or more biologically active fragments or derivatives of agnoprotein, such that growth of cells of the cancer or non-cancerous proliferative disorder is inhibited.

The invention also provides a pharmaceutical composition for treating a subject having a cancer or a non-cancerous proliferative disorder, comprising agnoprotein, or a biologically active fragment or derivative of agnoprotein, and a pharmaceutically acceptable carrier.

The invention further provides a pharmaceutical composition for treating a subject having a cancer or a non-cancerous proliferative disorder, comprising a nucleic acid sequence encoding agnoprotein, or a biologically active fragment or derivative of agnoprotein, and a pharmaceutically acceptable carrier.

Amino Acid Abbreviations

The nomenclature used to describe the peptide compounds of the present invention follows the conventional practice wherein the amino group is presented to the left and the carboxy group to the right of each amino acid residue. In the formulae representing selected specific embodiments of the present invention, the amino-and carboxy-terminal groups, although not specifically shown, will be understood to be in the form they would assume at physiologic pH values, unless otherwise specified. In the amino acid structure formulae, each residue is generally represented by a one-letter or three-letter designation, corresponding to the trivial name of the amino acid, in accordance with the following schedule:

| | | |
|---|---|---|
| A | Alanine | Ala |
| C | Cysteine | Cys |
| D | Aspartic Acid | Asp |
| E | Glutamic Acid | Glu |
| F | Phenylalanine | Phe |
| G | Glycine | Gly |
| H | Histidine | His |
| I | Isoleucine | Ile |
| K | Lysine | Lys |
| L | Leucine | Leu |
| M | Methionine | Met |
| N | Asparagine | Asn |
| P | Proline | Pro |
| Q | Glutamine | Gln |
| R | Arginine | Arg |
| S | Serine | Ser |

-continued

| | | |
|---|---|---|
| T | Threonine | Thr |
| V | Valine | Val |
| W | Tryptophan | Trp |
| Y | Tyrosine | Tyr |

Definitions

The expression "amino acid" as used herein is meant to include both natural and synthetic amino acids, and both D and L amino acids. "Standard amino acid" means any of the twenty standard L-amino acids commonly found in naturally occurring peptides. "Nonstandard amino acid" means any amino acid, other than the standard amino acids, regardless of whether it is prepared synthetically or derived from a natural source. As used herein, "synthetic amino acid" also encompasses chemically modified amino acids, including but not limited to salts, amino acid derivatives (such as amides), and substitutions. Amino acids contained within the peptides of the present invention, and particularly at the carboxy- or amino-terminus, can be modified by methylation, amidation, acetylation or substitution with other chemical groups which can change the peptide's circulating half life without adversely affecting their biological activity. Additionally, a disulfide linkage can be present or absent in the peptides of the invention.

Amino acids have the following general structure:

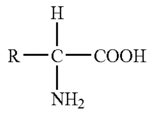

Amino acids are classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group.

As used herein, "agnoprotein" means the approximately 60-75 amino acid protein produced from the gene in the late leader region of a polyoma virus, which is located just upstream of the VP2 structural gene. Agnoproteins useful in the practice of the present invention are "biologically active" as defined herein, and have at least about 50% sequence identity, preferably at least about 60% sequence identity, for example 63% or 64% sequence identity, to SEQ ID NO: 1. More preferably, agnoproteins useful in the invention are biologically active as defined herein and have at least about 80% sequence identity, for example 83% or 84% sequence identity, with SEQ ID NO: 1. Particularly preferred agnoproteins are biologically active as defined herein and have 90%, 95% or 98% sequence identity with SEQ ID NO: 1.

"Biologically active" with respect to agnoprotein, or fragments or derivatives of agnoprotein, means the ability of the compound to inhibit the growth of NIH-3T3 cells according to the in vitro cell growth assays given in Example 2 below. Agnoproteins useful in the practice of the present invention specifically include agnoproteins from JCV, BK and SV40 polyoma virus strains.

"Isolated" means altered or removed from the natural state through the actions of a human being. For example, a nucleic acid sequence or a peptide naturally present in a living animal is not "isolated," but the same nucleic acid or peptide partially or completely separated from the coexisting materials of its natural state is "isolated." An isolated nucleic acid sequence or protein can exist in substantially purified form, or can exist in a non-native environment such as, for example, a host cell.

As used herein, "protecting group" with respect to a terminal amino group of a peptide means any of the various amino-terminal protecting groups traditionally employed in peptide synthesis. Such protecting groups include, for example, acyl protecting groups such as formyl, acetyl, benzoyl, trifluoroacetyl, succinyl, and methoxysuccinyl; aromatic urethane protecting groups such as benzyloxycarbonyl; and aliphatic urethane protecting groups, for example, tert-butoxycarbonyl or adamantyloxycarbonyl. See Gross and Mienhofer, eds., *The Peptides*, vol. 3, pp. 3-88 (Academic Press, New York, 1981) for suitable protecting groups.

As used herein, "protecting group" with respect to a terminal carboxy group of a peptide means any of various carboxyl-terminal protecting groups traditionally employed in peptide synthesis. Such protecting groups include, for example, tert-butyl, benzyl or other acceptable groups linked to the terminal carboxyl group through an ester or ether bond.

"Derivative" includes any naturally occurring or purposefully generated agnoprotein which is characterized by single or multiple amino acid substitutions, deletions, additions, or replacements. Such derivatives include (a) derivatives in which one or more amino acid residues of agnoprotein are substituted with conservative or non-conservative amino acids; (b) derivatives in which one or more amino acids are added; (c) derivatives in which one or more of the amino acids include a substituent group; (d) derivatives in which agnoprotein or a portion thereof is fused to another peptide (e.g., serum albumin or protein transduction domain); (e) derivatives in which one or more nonstandard amino acid residues (i.e., those other than the 20 standard L-amino acids found in naturally occurring proteins) are incorporated or substituted into the agnoprotein sequence; and (f) derivatives in which one or more nonamino acid linking groups are incorporated into or replace a portion of agnoprotein.

"Peptide" and "protein" are used interchangeably, and refer to a compound comprised of at least two amino acid residues covalently linked by peptide bonds or modified peptide bonds (e.g., peptide isosteres). No limitation is placed on the maximum number of amino acids which can comprise a protein or peptide. The amino acids comprising the peptides or proteins described herein and in the appended claims are understood to be either D or L amino acids with L amino acids being preferred. The amino acid comprising the peptides or proteins described herein can also be modified either by natural processes, such as posttranslational processing, or by chemical modification techniques which are well known in the art. Modifications can occur anywhere in a peptide, including the peptide backbone, the amino acid side-chains and the amino or carboxyl termini. It is understood that the same type of modification can be present in the same or varying degrees at several sites in a given peptide. Also, a given peptide can contain many types of modifications. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, PROTEINS—STRUCTURE AND MOLECULAR PROPERTIES, 2nd Ed., T. E. Creighton, W. H. Freeman and Company, New York, 1993 and Wold, F., Posttranslational Protein Modifications: Perspectives and Prospects, pgs. 1-12 in POSTTRANSLATIONAL COVALENT MODIFICATION OF PROTEINS, B. C. Johnson, Ed., Academic Press, New York, 1983; Seifter et al., "Analysis for protein modifications and nonprotein cofactors", Meth Enzymol (1990) 182:626-646 and Rattan et al., "Protein Synthesis: Posttranslational Modifications and Aging", Ann NY Acad Sci (1992) 663:48-62.

"Variant" as the term is used herein, is a nucleic acid sequence or peptide that differs from a reference nucleic acid sequence or peptide respectively, but retains essential properties of the reference molecule. Changes in the sequence of a nucleic acid variant can not alter the amino acid sequence of a peptide encoded by the reference nucleic acid, or can result in amino acid substitutions, additions, deletions, fusions and truncations. Changes in the sequence of peptide variants are typically limited or conservative, so that the sequences of the reference peptide and the variant are closely similar overall and, in many regions, identical. A variant and reference peptide can differ in amino acid sequence by one or more substitutions, additions, deletions in any combination. A variant of a nucleic acid or peptide can be a naturally occurring such as an allelic variant, or it can be a variant that is not known to occur naturally. Non-naturally occurring variants of nucleic acids and peptides can be made by mutagenesis techniques or by direct synthesis.

As used herein, "sequence identity" with respect to a reference peptide can be computed by using the BLASTP and TBLASTN programs which employ the BLAST (basic local alignment search tool) 2.0.14 algorithm; BLASTP and TBLASTN settings to be used in such computations are indicated in Table 1 below. Amino acid sequence identity is reported under "Identities" by the BLASTP and TBLASTN programs. Techniques for computing amino acid sequence identity are well known to those skilled in the art, and the use of the BLAST algorithm is described in Altschul et al. (1990), *J. Mol. Biol.* 215: 403-10 and Altschul et al. (1997), *Nucleic Acids Res.* 25:3389-3402, the disclosures of which are herein incorporated by reference in their entirety.

TABLE 1

Settings to be used for the computation of amino acid sequence identity with BLASTP and TBLASTN programs utilizing the BLAST 2.0.14 algorithm.

| | |
|---|---|
| Expect Value | 10 |
| Filter | Low complexity filtering using SEG program* |
| Substitution Matrix | BLOSUM62 |
| Gap existence cost | 11 |
| Per residue gap cost | 1 |
| Lambda ratio | 0.85 |
| Word size | 3 |

*The SEG program is described by Wootton and Federhen (1993), Comput. Chem. 17: 149-163.

"Sequence identity" with respect to a reference nucleic acid sequence can be determined by comparing the sequence identity of two sequences, for example by physical/chemical methods (i.e., hybridization) or by sequence alignment via computer algorithm. Suitable nucleic acid hybridization conditions to determine if a nucleic acid sequence possesses the required sequence identity to a reference nucleic acid sequence are: 7% sodium dodecyl sulfate (SDS), 0.5 M $NaPO_4$, 1 mM EDTA at 50° C. with washing in 2× standard saline citrate (SSC), 0.1% SDS at 50° C.; preferably in 7% (SDS), 0.5 M $NaPO_4$, 1 mM EDTA at 50° C. with washing in 1×SSC, 0.1% SDS at 50° C. Suitable computer algorithms to determine substantial similarity between two nucleic acid sequences include, but are not limited to: GCS program package (Devereux et al. (1984), *Nucl. Acids Res.* 12: 387), and the BLASTN or FASTA programs (Altschul et al. (1990), *J. Mol. Biol.* 215: 403). The default settings provided with these programs are adequate for determining substantial similarity of nucleic acid sequences for purposes of the present invention.

"Substantially purified" refers to a peptide or nucleic acid sequence which is substantially homogenous in character due to the removal of other compounds (e.g., other peptides, nucleic acids, carbohydrates, lipids) or other cells originally present. "Substantially purified" is not meant to exclude artificial or synthetic mixtures with other compounds, or the presence of impurities which do not interfere with biological activity, and which can be present, for example, due to incomplete purification, addition of stabilizers, or formulation into a pharmaceutically acceptable preparation.

DETAILED DESCRIPTION OF THE INVENTION

Figure 1A:
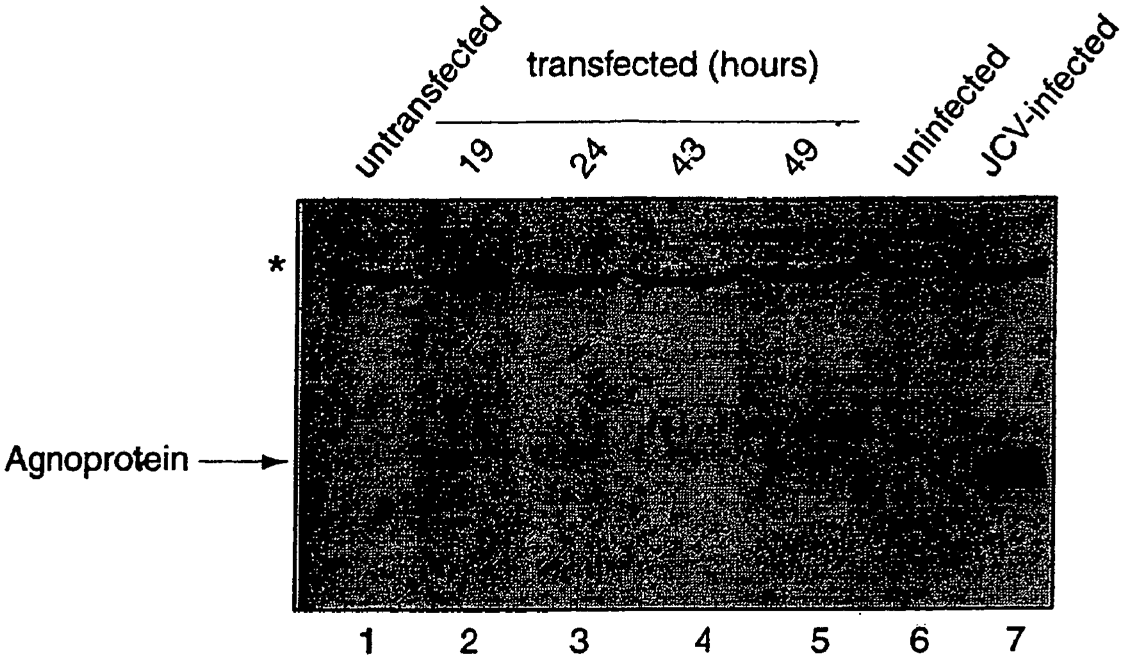
FIG. 1A is Western blot analysis of protein extracts from U-87MG cells transfected with a plasmid expressing agnoprotein. Lane 1 represents approximately 50 μg of total protein extract from untransfected cells. Lanes 2-5 represent, respectively, 50 μg of total protein extract from cells transfected with pCMV-agnoprotein at 19, 24, 43, and 49 hours after transfection. Lanes 6 and 7 represent extracts from uninfected and JCV-infected human astrocytes, respectively. The position of the agnoprotein is shown by an arrow. The asterisk shows the position of a non-specific band.

Introduction of agnoprotein into a cell, in the absence of other polyoma viral proteins, inhibits growth of the cell. Without wishing to be bound by any particular theory, it appears that agnoprotein deregulates cell growth by delaying progression of cells through the various phases of the cell cycle. The growth of both normally and abnormally proliferating cells can be inhibited with agnoprotein.

Agnoprotein from any species and strain of polyoma virus can be used in the practice of the present invention. Preferred agnoproteins are those derived from JCV, in particular from the Mad-1 strain of JCV. The agnoprotein from JCV strain Mad1 is a 71 amino acid protein with the following primary sequence:

```
(SEQ ID NO:1)
MVLRQLSRKASVKVSKTWSGTKKRAQRILIFLLEFLLDFCTGEDS
VDGKKRQRHSGLTEQTYSALPEPKAT
```

The nucleic acid sequence encoding SEQ ID NO: 1 is given in SEQ ID NO: 2.

Other JCV agnoproteins known in the art include those disclosed in GenBank records Accession No. AF187236 (SEQ ID NO: 3), Accession No. AF281599 (SEQ ID NO: 4), Accession No. AF187234 (SEQ ID NO: 5), Accession No. AF295737 (SEQ ID NO: 6) and Accession No. AF295739 (SEQ ID NO: 7), the entire disclosures of which are herein in incorporated by reference. The nucleic acid sequences encoding these agnoproteins are given, respectively, in SEQ ID NO: 8, SEQ ID NO: 9, SEQ ID NO: 10, SEQ ID NO: 11, and SEQ ID NO: 12.

See also Cubitt C L et al. (2001), *J. Neurovirol.* 7: 339-344, the disclosure of which is herein incorporated by reference, in which predicted agnoprotein amino acid sequences for 100 JCV strains were analyzed to produce the following agnoprotein consensus sequence:

(SEQ ID NO:13)

M-V-L-R-Q-L-S-R-K-A-S-V-K-V-S-K-T-W-S-G-T-K-K-R-A-Q-R-I-L-
I-F-L-L-E-F-L-L-D-F-C-T-G-E-D-$X_1$-V-D-G-K-K-R-Q-$X_2$-H-$X_3$-$X_4$-$X_5$-$X_6$-$X_7$-
$X_8$-$X_9$-$X_{10}$-$X_{11}$-A-L-P-E-P-K-A-$X_{12}$ wherein $X_1$ is serine or arginine;
$X_2$ is lysine or arginine;
$X_3$ is serine or arginine;
$X_4$ is glycine or no amino acid;
$X_5$ is leucine or no amino acid;
$X_6$ is threonine or no amino acid;
$X_7$ is glutamine, glutamic acid, or no amino acid;
$X_8$ is glutamine or no amino acid;
$X_9$ is threonine, arginine, lysine or no amino acid;
$X_{10}$ is tyrosine or no amino acid;
$X_{11}$ is serine or glycine; and
$X_{12}$ is threonine or lysine.

A protein comprising SEQ ID NO: 13 is considered an agnoprotein, and can be used to inhibit growth of cells according to the present invention.

Agnoprotein from human BK polyoma virus strains, or from SV40 polyoma virus strains, are also known. Examples of BK virus agnoproteins are found in GenBank record Accession Nos. M23122 (SEQ ID NO: 14) and D00678 (SEQ ID NO: 15), and a partial BK virus agnoprotein sequence is found in Accession No. AF442903 (SEQ ID NO: 16), the disclosures of which are herein incorporated by reference. An example of SV40 agnoprotein is found in GenBank record Accession No. M99359 (SEQ ID NO: 17), the disclosure of which is herein incorporated by reference.

Nucleic acid sequences encoding the BK virus and SV40 agnoproteins described above are given in SEQ ID NO: 18, SEQ ID NO: 19, SEQ ID NO: 20, and SEQ ID NO: 21 respectively.

Agnoproteins can be isolated from mammalian cells infected with polyoma viruses according to known techniques. Agnoproteins can also be produced synthetically by any known means, including synthesis by biological systems and by chemical methods.

Biological synthesis of peptides is well known in the art, and includes the transcription and translation of a naturally-occurring or synthetic gene encoding agnoprotein sequences. These nucleic acids can be subcloned into an appropriate plasmid expression vector for propagation and expression in an appropriate host. For example, techniques for cloning and expression of the agnoprotein of SEQ ID NO: 1 are described in the Examples below.

Other techniques used to construct nucleic acid sequences and plasmid expression vectors, transfect host cells, and express a nucleic acid sequence of interest are widely practiced in the art, and practitioners of ordinary skill are familiar with the standard resource materials which describe specific conditions and procedures. For example, general methods for the cloning and expression of recombinant molecules are described in Sambrook et al., *Molecular Cloning*, Cold Spring Harbor Laboratories, 1982; and in Ausubel, *Current Protocols in Molecular Biology*, Wiley and Sons, 1987, the disclosures of which are incorporated herein by reference.

Agnoprotein produced from an expression vector can be obtained from the host cell by cell lysis, or by using heterologous signal sequences fused to the expressed protein which cause secretion of the protein into the surrounding medium. Preferably, the signal sequence is designed so that it can be removed by chemical or enzymatic cleavage, as is known in the art. The agnoprotein thus produced can then be purified in a manner similar to that utilized for isolation of agnoprotein from isolated from mammalian cells infected with polyoma viruses.

Chemical peptide synthesis techniques suitable for directly synthesizing agnoprotein, including manual and automated techniques, are also well-known to those of ordinary skill in the art. For example, agnoprotein can be synthesized de novo using conventional solid phase synthesis methods. In such methods, the peptide chain is prepared by a series of coupling reactions in which the constituent amino acids are added to the growing peptide chain in the desired sequence. The use of various N-protecting groups, e.g., the carbobenzyloxy group or the t-butyloxycarbonyl group; various coupling reagents e.g., dicyclohexylcarbodiimide or carbonyldimidazole; various active esters, e.g., esters of N-hydroxyphthalimide or N-hydroxy-succinimide; and the various cleavage reagents, e.g., trifluoroactetic acid (TFA), HCl in dioxane, boron tris-(trifluoracetate) and cyanogen bromide; and reaction in solution with isolation and purification of intermediates are methods well-known to those of ordinary skill in the art.

A preferred chemical peptide synthesis method follows conventional Merrifield solid phase procedures well known to those skilled in the art. Additional information about solid phase synthesis procedures can be had by reference to Steward and Young, *Solid Phase Peptide Synthesis*, W.H. Freeman & Co., San Francisco, 1969; the review chapter by Merrifield in *Advances in Enzymology* 32:221-296, (Nold FF, ed.), Interscience Publishers, New York, 1969; and Erickson and Merrifield (1990), *The Proteins* 2:61-64, the entire disclosures of which are incorporated herein by reference. Crude peptide preparations resulting from solid phase syntheses can be purified by methods well known in the art, such as preparative HPLC. The amino-terminus can be protected according to the methods described for example by Yang et al., *FEBS Lett.* 272:61-64 (1990), the entire disclosure of which is herein incorporated by reference.

Agnoproteins for use in the present invention can also comprise a label a (e.g., substances which are magnetic resonance active; radiodense; fluorescent; radioactive; detectable by ultrasound; detectable by visible, infrared or ultraviolet light) so that the agnoprotein can be detected. Suitable labels include, for example, fluorescein isothiocyanate (FITC); peptide chromophores such as phycoerythrin or phycocyanin and the like; bioluminescent peptides such as the luciferases originating from *Photinus pyrali*; fluorescent proteins originating from *Renilla reniformi*; and radionuclides such as $^{32}P$, $^{33}P$, 35S, $I^{125}$ or $^{123}I$. For example, the label can comprise an $NH_2$-terminal fluorescein isothiocyanate (FITC)-Gly-Gly-Gly-Gly motif that is conjugated to a protein transduction domain.

Methods of modifying peptide sequences such as agnoprotein with labels are well known to those skilled in the art. For example, methods of conjugating fluorescent compounds such as fluorescein isothiocyanate to short peptides are described in Danen et al., *Exp. Cell Res.*, 238:188-86 (1998), the entire disclosure of which is incorporated herein by reference.

Biologically active fragments of agnoprotein can also be used in the present methods. Biologically active agnoprotein fragments according to the invention can be obtained, for example, by chemical or enzymatic fragmentation of larger natural or synthetic agnoproteins, or by biological or chemical syntheses as described above.

Biologically active derivatives of agnoprotein can also be used in the present methods. The techniques for obtaining such derivatives are known to persons having ordinary skill in the art and include, for example, standard recombinant nucleic acid techniques, solid phase peptide synthesis techniques and chemical synthetic techniques as described above. Linking groups can also be used to join or replace portions of agnoprotein and other peptides. Linking groups include, for example, cyclic compounds capable of connecting an amino-terminal portion and a carboxyl terminal portion of agnoprotein. Techniques for generating derivatives are also described in U.S. Pat. No. 6,030,942 the entire disclosure of which is herein incorporated by reference (derivatives are designated "peptoids" in the U.S. Pat. No. 6,030,942). Agnoprotein derivatives can also comprise labels such as are described above.

Agnoprotein derivatives also include fusion peptides in which a portion of the fusion peptide has a substantially similar amino acid sequence to agnoprotein. Such fusion peptides can be generated by techniques well-known in the art, for example by subcloning nucleic acid sequences encoding an agnoprotein and a heterologous peptide sequence into the same expression vector, such that the agnoprotein and the heterologous sequence are expressed together in the same protein. The heterologous sequence can comprise a peptide leader sequence that directs entry of the expressed protein into a cell. Such leader sequences include "protein transduction domains" or "PTDs", which are discussed in more detail below.

A preferred agnoprotein derivative comprises the JCV agnoprotein described in Jobes D V et al. (1999), *J. Human Virol.* 2(6): 350-358, the disclosure of which is herein incorporated by reference, which has a 7-amino acid deletion in the C-terminal region (SEQ ID NO: 22). The nucleic acid sequence encoding SEQ ID NO: 22 is given in SEQ ID NO: 23.

The agnoproteins and biologically active fragments and derivatives of agnoproteins described above are also referred to hereunder as "compounds of the invention."

The compounds of the invention can be modified to enhance their entry into cells. For example, the compounds of the invention can be encapsulated in a liposome prior to being administered. The encapsulated compounds are delivered directly into the abnormally proliferating cells by fusion of the liposome to the cell membrane. Reagents and techniques for encapsulating the present compounds in liposomes are well-known in the art, and include, for example, the ProVectin™ Protein Delivery Reagent from Imgenex.

In a preferred embodiment, the compounds of the invention are modified by associating the compounds with a peptide leader sequence known as a "protein transduction domain" or "PTD." These sequences direct entry of the compound into abnormally proliferating cells by a process known as "protein transduction." See Schwarze et al. (1999), *Science* 285: 1569-1572.

PTDs are well-known in the art, and can comprise any of the known PTD sequences including, for example, arginine-rich sequences such as a peptide of nine to eleven arginine residues optionally in combination with one to two lysines or glutamines as described in Guis et al. (1999), *Cancer Res.* 59: 2577-2580, the disclosure of which is herein incorporated by reference. Preferred are sequences of eleven arginine residues or the $NH_2$-terminal 11-amino acid protein transduction domain from the human immunodeficiency virus TAT protein (SEQ ID NO: 24). Other suitable leader sequences include, but are not limited to, other arginine-rich sequences; e.g., 9 to 10 arginines, or six or more arginines in combination with one or more lysines or glutamines. Such leader sequences are known in the art; see, e.g., Guis et al. (1999), supra. Preferably, the PTD is designed so that it is cleaved from the compound upon entry into the cell. A PTD can be located anywhere on the agnoprotein, or fragment or derivative of agnoprotein, that does not disrupt the compound's biological activity, and is preferably located at the N-terminal end.

Kits and methods for constructing fusion proteins comprising a protein of interest (e.g., agnoprotein) and a PTD are known in the art; for example the TransVector™ system (Q-BIOgene), which employs a 16 amino acid peptide called "Penetratin™" corresponding to the *Drosophila* antennapedia DNA-binding domain; and the Voyager system (Invitrogen Life Technologies), which uses the 38 kDa VP22 protein from Herpes Simplex Virus-1.

Agnoprotein, or biologically active fragments or derivatives of agnoprotein, can inhibit proliferation of normal and abnormally proliferating cells. Abnormally proliferating cells include cells from cancer types of diverse histologic subtype and origin, such as those listed and described in the National Cancer Institute's "CancerNet," which is herein incorporated by reference in its entirety.

For example, the compounds of the invention can be used to inhibit the proliferation of primary or metastatic tumor or neoplastic cells from cancers of at least the following histologic subtypes: sarcoma (cancers of the connective and other tissue of mesodermal origin); melanoma (cancers deriving from pigmented melanocytes); carcinoma (cancers of epithelial origin); adenocarcinoma (cancers of glandular epithelial origin); cancers of neural origin (glioma/glioblastoma and astrocytoma); and hematological neoplasias, such as leukemias and lymphomas (e.g., acute lymphoblastic leukemia, chronic lymphocytic leukemia, and chronic myelocytic leukemia).

The compounds of the invention can also be used to inhibit the proliferation of primary or metastatic tumor or neoplastic cells from cancers having their origin in at least the following organs or tissues, regardless of histologic subtype: breast; tissues of the male and female urogenital system (e.g. ureter, bladder, prostate, testis, ovary, cervix, uterus, vagina); lung; tissues of the gastrointestinal system (e.g., stomach, large and small intestine, colon, rectum); exocrine glands such as the pancreas and adrenals; tissues of the mouth and esophagus; brain and spinal cord; kidney (renal); pancreas; hepatobiliary system (e.g., liver, gall bladder); lymphatic system; smooth and striated muscle; bone and bone marrow; skin; and tissues of the eye.

Furthermore, the compounds of the invention can be used to inhibit the proliferation of cells from cancers or tumors in any prognostic stage of development, as measured, for example, by the "Overall Stage Groupings" (also called "Roman Numeral") or the Tumor, Nodes, and Metastases (TNM) staging systems. Appropriate prognostic staging systems and stage descriptions for a given cancer are known in the art, for example as described in the National Cancer Institute's "CancerNet," supra.

Agnoprotein, or biologically active fragments or derivatives of agnoprotein, can also be used to inhibit proliferation of cells from non-cancerous proliferative disorders. The non-cancerous proliferative disorders are characterized by cells which have escaped normal growth controls, but are not able to metastasize. Abnormally proliferating cells in such disorders typically form fibroid growths or benign tumors.

Examples of non-cancerous proliferative disorders include any benign skin lesion or condition involving the uncontrolled growth of fibroblasts, hemangiomatosis in newborn; secondary progressive multiple sclerosis; chronic progressive myelodegenerative disease; neurofibromatosis; ganglioneuromatosis; keloid formation; Paget's Disease of the bone; fibrocystic disease (e.g., of the breast, lungs, or uterus); sarcoidosis; Peronies' and Duputren's fibrosis, cirrhosis, atherosclerosis and vascular restenosis.

Preferably, the compounds of the invention are used to treat a subject having abnormally proliferating cells deriving from a cancer or a non-cancerous proliferative disorder. In treating subjects with such conditions, one or more compounds of the invention are administered to a subject in an amount effective to inhibit proliferation of abnormally proliferating cells (the "effective amount"). The subject can be any animal, preferably a mammal, particularly preferably a human being.

As used herein, to "inhibit the proliferation of an abnormally proliferating cell" means to kill the cell, or permanently or temporarily arrest the growth of the cell.

Inhibition of proliferation can be inferred if the number of abnormally proliferating cells in the subject remains constant or decreases after administration of the present compounds. Inhibition of proliferation can also be inferred if the absolute number of abnormally proliferating cells increases, but the rate of growth of a tissue mass decreases. As used herein, a "tissue mass" is any localized collection of abnormally proliferating cells in a subject's body; for example a tumor, fibroid body, restenotic plaque, and the like. The number of abnormally proliferating cells in a subject's body can be determined by direct measurement (e.g., calculating the concentration of leukemic cells in the blood or bone marrow) or by estimation from the size of a tissue mass.

The size of a tissue mass can be ascertained by direct visual observation or by diagnostic imaging methods such as X-ray, magnetic resonance imaging, ultrasound, and scintigriphy. Diagnostic imaging methods used to ascertain size of a tissue mass can be employed with or without contrast agents, as is known in the art. The size of a tissue mass can also be ascertained by physical means, such as palpation of the tissue mass or measurement of the tissue mass with a measuring instrument such as a caliper.

Agnoprotein, or biologically active fragments or derivatives of agnoprotein, can be administered to a subject by any technique designed to expose abnormally proliferating cells in the subject's body to the compounds, such that the compounds are taken up by the cells. For example, the compounds of the invention can be administered by any enteral or parenteral route. Parenteral administration is preferred.

Suitable parenteral administration methods include intravascular administration (e.g. intravenous bolus injection, intravenous infusion, intra-arterial bolus injection, intra-arterial infusion and catheter instillation into the vasculature); peri- and intra-tissue injection (e.g. peri-turnoral and intratumoral injection); subcutaneous injection or deposition including subcutaneous infusion (such as by osmotic pumps); and direct application to the abnormally proliferating cells or to tissue comprising the abnormally proliferating cells, for example by a catheter or other placement device. It is preferred that subcutaneous injections or infusions be given in the area near the abnormally proliferating cells, particularly if the cells are on or near the skin.

The compounds of the invention can be injected in a single dose or in multiple doses. Infusion of the compounds of the invention can comprise a single sustained dose over a prolonged period of time or multiple infusions. Direct injection into tissue comprising the abnormally proliferating cells is preferred.

An effective amount of the compounds of the invention can be based on the approximate weight of the tissue mass to be treated. The approximate weight of a tissue mass can be determined by calculating the approximate volume of the tissue mass, wherein one cubic centimeter of tissue mass volume is roughly equivalent to one gram. Where more than one compound of the invention is administered, the effective amount represents the cumulative total of the administered compounds.

An effective amount of the compounds of the invention based on the weight of a tissue mass can be at least about 10 μg compound/gram of tissue mass, and is preferably between about 10-1000 μg compound/gram of tissue mass. More preferably, the effective amount is at least about 60 μg compound/gram of tissue mass. Particularly preferably, the effective amount is at least about 100 μg compound/gram of tissue mass. It is preferred that effective amounts based on the weight of the tissue mass be injected directly into the tissue mass.

An effective amount of the compounds of the invention can also be based on the approximate or estimated body weight of the subject to be treated. Preferably, such effective amounts are administered systemically; e.g. by intravascular injections and infusions, subcutaneous depositions or infusions, or intramuscular or intraperitoneal administrations. Where more than one compound of the invention is administered, the effective amount represents the cumulative total of the administered compounds.

For example, an effective amount of the compounds of the invention administered by single intravascular injection in humans (assuming a 60 kg subject) can range from about 5-3000 μg compound/kg of body weight, is preferably between about 700-1000 μg compound/kg of body weight, and is more preferably greater than about 1000 μg compound/kg of body weight.

An effective amount of the compounds of the invention used for multiple intravascular injections can be the same or lower than that used for single intravascular injections. For example, an effective amount for multiple intravascular injection in humans is preferably greater than about 250 μg compound/kg body weight, and is more preferably greater than about 500 μg compound/kg body weight.

An effective amount of the compounds of the invention administered by single sustained intravascular infusion can be the same as that used for single and multiple intravascular injections, but can also be lower. For example, an effective amount for single sustained infusions in humans is preferably greater than about 90 μg compound/kg body weight, and is more preferably greater than about 100 μg compound/kg body weight.

An effective amount of the compounds of the invention administered by multiple sustained intravascular infusions can be the same as that used for single and multiple injections and single sustained intravascular infusion, but can also be lower. For example, an effective amount for multiple sustained intravascular infusions in humans is preferably greater than about 35 μg/kg, and is more preferably greater than about 50 μg/kg.

An effective amount of the compounds of the invention administered by subcutaneous, intramuscular or intraperitoneal routes can be the same as that used for intravascular administration, but is preferably between about 200 and 1000 μg compound/kg body weight. More preferably, the effective amount is greater than 500 μg compound/kg of body weight.

An effective amount of the compounds of the invention can also be based on the approximate surface area of the subject to be treated. Effective amounts based on surface area are typically expressed in terms of μg compound/square meter of surface area ($m^2$). It is preferred to base effective amounts on the surface area of a subject, because better inter-species comparisons can be made. Also, effective amounts based on surface area allow amounts to be determined for human adults and children without further adjustment. The assumptions underlying the inter-species and adult to child conversion of effective amounts based on surface area are found in E J Freireich et al., (1966), *Cancer Chemotherapy Reports* 50: 219-244, the disclosure of which is herein incorporated by reference in its entirety.

Table 2 provides approximate surface area-to-weight ratios for various species. The surface area-to-weight ratio can be used to convert effective amounts based on body weight (expressed in μg/kg) to effective amounts based on surface area (expressed in μg/$m^2$). The surface area-to-weight ratio is also used to calculate the conversion factors found in Table 3, which can be used to convert effective amounts expressed in terms of μg/kg from one species to another.

TABLE 2

Surface Area to Weight Ratios of Various Species*

| Species Body | Weight (kg) | Surface Area ($m^2$) | Surface Area to Weight Ratio (kg/$m^2$) |
|---|---|---|---|
| Mouse | 0.02 | 0.0066 | 3.0 |
| Rat | 0.15 | 0.025 | 5.9 |
| Monkey | 3 | 0.24 | 12 |
| Dog | 8 | 0.40 | 20 |
| Human | | | |
| child | 20 | 0.80 | 25 |
| adult | 60 | 1.6 | 37 |

*Adapted from DeVita, VT, "Principles of Chemotherapy," pgs. 292-3, in Cancer: Principles and Practice of Oncology, (3rd edit., DeVita VT, Hellman S, and Rosenberg SA, eds.), 1989, J. B. Lipincott Co., Phila., PA.

As shown in Table 2, to convert an effective amount based on body weight in μg/kg for any given species to the equivalent effective amount based on surface area (in μg/$m^2$), multiply the effective amount based on body weight by the approximate surface area to weight ratio. For example, in the adult human 100 μg/kg is equivalent to 100 μg/kg×37 kg/$m^2$=3700 μg/$m^2$.

Table 3 gives approximate factors for converting effective amounts expressed in terms of μg/kg from one species to an equivalent surface area effective amount expressed in the same units (μg/kg) for another species. For example, given a dose of 50 μg/kg in the mouse, the appropriate dose in man (assuming equivalency on the basis of μg/$m^2$) is 50 μg/kg× 1/12=4.1 μg/kg. For the present invention, equivalency on the basis of μg/$m^2$ is assumed.

TABLE 3

Equivalent Surface Area Dosage Conversion Factors*

| | Mouse (20 g) | Rat (150 g) | Monkey (3 kg) | Dog (8 kg) | Man (60 kg) |
|---|---|---|---|---|---|
| Mouse | 1 | 1/2 | 1/4 | 1/6 | 1/12 |
| Rat | 2 | 1 | 1/2 | 1/4 | 1/7 |
| Monkey | 4 | 2 | 1 | 3/5 | 1/3 |
| Dog | 6 | 4 | 5/3 | 1 | 1/2 |
| Man | 12 | 7 | 3 | 2 | 1 |

*Adapted from DeVita, VT, "Principles of Chemotherapy," pgs. 292-3, in Cancer: Principles and Practice of Oncology, (3rd edit., DeVita V T, Hellman S, and Rosenberg S A, eds.), 1989, J. B. Lipincott Co., Phila., PA.

An effective amount of the compounds of the invention based on surface area is preferably administered systemically, as described above for effective amounts based on body weight. However, effective amounts based surface area can also be administered by peri- or intra-tissue mass injection or by direct application to the tissue mass. Where more than one compound of the invention is administered, the effective amount represents the cumulative total of the administered compounds.

Agnoprotein, and biologically active fragments and derivatives of agnoprotein, can also be administered to a subject by transfection of the abnormally proliferating cells in the subject's body with one or more nucleic acid sequences encoding a compound of the invention. Preferably, the nucleic acid sequences comprise a plasmid expression vector. Such plasmids can be generated by recombinant nucleic acid and molecular cloning techniques well-known in the art, as discussed above.

Transfection methods for eukaryotic cells are well known in the art, and include, for example, direct injection of the nucleic acid into the nucleus or pronucleus; electroporation; liposome transfer; receptor mediated nucleic acid delivery, bioballistic or particle acceleration; calcium phosphate precipitation, and transfection mediated by viral vectors.

For example, the transfection is performed with a liposomal transfer compound, e.g., DOTAP (N-[1-(2,3-dioleoyloxy)propyl]-N,N,N-trimethyl-ammonium methylsulfate, Boehringer—Mannheim) or an equivalent, such as LIPOFECTIN. The amount of nucleic acid used is not critical to the practice of the invention; acceptable results can be achieved with 10 mM nucleic acid/$10^5$ cells. A ratio of about 500 nanograms of plasmid vector in 3 micrograms of DOTAP per $10^5$ cells can be used. Other suitable methods for the construction and propagation of plasmid vectors capable of expressing the present compounds, and techniques for transfecting such vectors into eukaryotic cells so that the compounds are expressed, are known in the art. A preferred transfection method is the calcium phosphate precipitation method described in the Examples below.

The present invention also provides pharmaceutical formulations for treating cancer or non-cancerous proliferative disorders. The pharmaceutical compositions of the invention comprise one or more agnoproteins, or one or more biologically active fragments or derivatives of agnoprotein. The pharmaceutical formulations of the present invention can also comprise one or more nucleic acids encoding an agnoprotein or a biologically active fragment or derivative of agnoprotein.

Pharmaceutical formulations of the present invention are characterized as being at least sterile and pyrogen-free. As used herein, "pharmaceutical formulations" include formulations for human and veterinary use. The present pharmaceutical formulations can be prepared by mixing agnoprotein, biologically active fragments or derivatives of agnoprotein, or nucleic acids encoding these compounds with a physiologically acceptable carrier medium to form solutions, suspensions or dispersions. Preferred physiologically acceptable carrier media are water or normal saline.

Pharmaceutical formulations of the invention can also comprise conventional pharmaceutical excipients and/or additives. Suitable pharmaceutical excipients include stabilizers, antioxidants, osmolality adjusting agents, buffers, and pH adjusting agents. Suitable additives include physiologically biocompatible buffers (e.g., tromethamine hydrochloride), additions (e.g., 0.01 to 10 mole percent) of chelants (such as, for example, DTPA or DTPA-bisamide) or calcium chelate complexes (as for example calcium DTPA, CaNaDTPA-bisamide), or, optionally, additions (e.g. 1 to 50 mole percent) of calcium or sodium salts (for example, calcium chloride, calcium ascorbate, calcium gluconate or calcium lactate). Pharmaceutical formulations of the invention can be prepared in a manner fully within the skill of the art.

The invention will now be illustrated with the following non-limiting examples.

EXAMPLES

General Experimental Procedures

The following general experimental procedures were used in the Examples discussed below.

Cell Culture and Transfection—Human astrocytoma cell line U-87MG (ATCC catalog no. HTB-14), human glioblastoma multiforme cell line T98G (ATCC catalog no. CRL-1960), mouse fibroblast NIH 3T3 cells (ATCC catalog no. CRL-1658), and cell line Saos-2 were maintained in Dulbecco's Modified Eagle's Medium (DMEM) supplemented with 10% fetal bovine serum (FBS). Transfections were performed on approximately 5-7×$10^5$ cells per 60 mm dish using the calcium phosphate precipitation method, according to the method of Graham FL and van der Eb A J (1973) *Virology* 52, 456-467, the entire disclosure of which is herein incorporated by reference. At 48 hours post-transfection, cells were harvested for protein extract preparation or were transferred to 100 mm plates containing DMEM plus 10% FBS and Geneticin at a concentration of 0.5 mg/ml for the selection of stably transfected cells.

Plasmids—The plasmids that were used in the various transfections were pCMV-agnoprotein, pCMV-GFP, pGEX-1λT-agnoprotein, pYFP-agnoprotein, pEYFP-N1, pTR (AAV)-Agno, and p21-luciferase.

pCMV-agnoprotein and pGEX-1λT-agnoprotein are described in Safak M et al. (2001) *J. Virol.* 75, 1476-1486, the entire disclosure of which is herein incorporated by reference.

pEGFP-N1 was obtained from Clontech.

pYFP-agnoprotein was created by PCR amplification of the gene encoding the agnoprotein from the plasmid pBJC (which contained the Mad-1 strain of JCV) using the following primers containing a BamHI and EcoRI site, respectively:

```
                                    (SEQ ID NO:25)
5'-ACGTCCAGGATCCATGGTTCTTCGCCAGCTGTCA-3'

                                    (SEQ ID NO:26)
5'-ACGTCCAGAATTCCTATGTAGCTTTTGGTTCAGG-3'
```

After gel purification, the amplicon was digested with BamHI and EcoRI and subcloned into the same sites of the pEYFP-N1 vector multiple cloning site (Clontech). All constructs were verified by sequencing. The pEYFP-N1 vector, which expresses only YFP, was used as a control.

pTR(AAV)-Agno was constructed by amplifying the sequence encoding the agnoprotein with the following primers, which contain NotI sites and create a T7 promoter for the amplicon:

```
5'-TATGCGGCCGCTAATACGACTCACTATAGG-3' (SEQ ID NO:27)

5'-TAGAATAGGGCCCTCTAGATGCATGCTCGA-3' (SEQ ID NO:28)
```

The amplicon was then digested with NotI and inserted into the NotI site of the pTR(AAV) vector. All constructs were verified by sequencing.

p21-luciferase was obtained from Dr. B. Sawaya, Center for Neurovirology and Cancer Biology, Temple University, Philadelphia, Pa.

Protein Extract Preparation—For protein extraction, cells were lysed for 20 min on ice in lysis buffer (20 mM Tris-HCl, pH 7.4; 150 mM NaCl; 0.5% NP40) containing 10 μg/ml leupeptin, 2 μg/ml aprotinin, 100 μg/ml PMSF, 100 μg/ml TPCK; and 10 μg/ml pepstatin. Cell debris was removed by centrifugation and the supernatant was collected for protein concentration by Bradford analysis (Bio-Rad, Hercules, Calif.).

Western Blot Analysis—Approximately 50 μg of the protein extracts were separated by SDS-PAGE (12% gel) and analyzed by Western blot using the specific antibodies set forth in the Examples below. Briefly, proteins resolved by SDS-PAGE were transferred to Optitran-supported nitrocellulose (Schleicher & Schuell) and blocked in PBS-T (PBS-0.1% Tween 20) containing 10% non-fat dry milk for 45 min. Blots were then incubated in primary antibody for two hours, washed 3×10 min in PBS-T, incubated with anti-mouse or anti-rabbit secondary antibody conjugated to horseradish peroxidase for an additional hour, followed by washing 3×10 min in PBS-T. Blots were developed with ECL-Plus (Amersham Pharmacia, Piscataway, N.J.) and detected by autoradiography.

Immunoprecipitation—150-500 μg of protein extracts were incubated with anti-p53 antibody overnight at 4° C., with rotation. This solution was then incubated with 30 μl of pre-washed protein A Sepharose for 2 hours at 4° C. to precipitate the protein complexes. The precipitated Sepharose A/protein complexes were washed twice in lysis buffer, resuspended in 10 μl of Laemmli sample buffer (62.5 mM Tris-HCl pH 6.8; 2% SDS; 25% glycerol; 0.01% Bromophenol Blue) (Biorad), and incubated for 15 min at room temperature. Samples were centrifuged, the supernatant was boiled at 95° C. for 10 min and resolved by SDS-PAGE followed by Western blot analysis as above, using anti-agnoprotein antibody.

H1 kinase assay—Approximately 200 μg of protein extract was immunoprecipitated with antibodies as specified in the Examples below. Approximately 30 μl of packed protein-A Sepharose beads in lysis buffer was added to the extracts and incubated at 4° C. for 3 hours. The immunoprecipitates were assayed for kinase activity for 30 min at 30° C., in assay buffer containing 5 μCi of [$\gamma^{32}P$]ATP, 5 μg of histone H1, 1 mM DTT, 10 mM $MgCl_2$, and 20 mM Tris (pH 7.4). The reaction was stopped by the addition of Laemmli sample buffer (Bio-Rad) and analyzed by SDS-PAGE followed by autoradiography.

Cell Proliferation and Flow Cytometry—Cells were plated in 35 mm petri dishes at a density of $1\times10^4$ cells/plate and maintained in DMEM plus 10% FBS. Cells were collected at various times and cell proliferation was assessed by determining total cell number by phase contrast microscopy.

For flow cytometry, cells were synchronized by serum starvation for 72 hrs. and then stimulated by the addition of growth media containing serum. At various times after serum stimulation, as indicated in the Examples, cells were collected by centrifugation and were resuspended in 300 μl of PBS containing 10 μg/ml of propidiun iodide and 250 μg/ml of RNase A. Samples were incubated at 37° C. for 30 min and kept at 4° C. until analyzed. Cells were analyzed by flow cytometry (i.e., fluorescence activated cell sorting, or "FACS") with a Becton Dickinson "FACScan" flow cytometer using the SOBR program.

In Vitro GST Pull-Down Assay—Three microliters of [$^{35}S$]-labeled in vitro translated p53 or agnoprotein were incubated with 5 μg of GST or fusion proteins, GST-agnoprotein or GST-p53 coupled to glutathione Sepharose beads in 300 μl of LB150 buffer (50 mM Tris-HCl, pH 7.4; 150 mM NaCl; 5 mM EDTA; 0.1% NP40) for one hour at 4° C., with continuous rocking. After incubation, the beads were precipitated and washed five times with LB150 buffer. The bound proteins were eluted with Laemmli sample buffer (BioRad), heated at 95° C. for 10 min, and resolved by SDS-PAGE. p53 or agnoprotein was detected by autoradiography.

Example 1

Expression of Agnoprotein in Glial Cells and Effect of Agnoprotein on Cell Cycle Progression U-87MG cells were transfected with the agnoprotein-expressing plasmid pCMV-agnoprotein, and the level of agnoprotein was determined at 19, 24, 43 and 49 hrs. post-transfection. Untransfected U-87MG cells were used as a control. As shown in FIG. 1A, Western blot analysis of protein extracts from control cells (lane 1) and transfected cells at the various time points (lanes 2-5) showed detectable levels of agnoprotein in transfected cells from 19 hours post-transfection, with accumulation of agnoprotein up to 49 hours post-transfection. FIG. 1A also shows a band corresponding to agnoprotein in normal human astrocytes infected with JCV at 15 days post-infection (lane 7), and its absence in uninfected cells (lane 6).

Figure 1B:
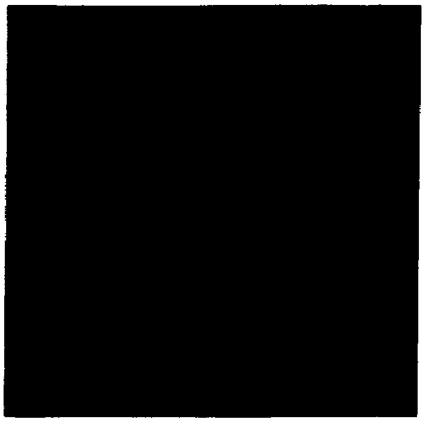
FIGS. 1B and 1C are photomicrographs showing U-87MG cells transfected with a plasmid expressing agnoprotein which were fixed and reacted, respectively, with preimmune or anti-agnoprotein antibodies at 24 hrs. post-transfection (original magnification 400×).
Figure 1C:
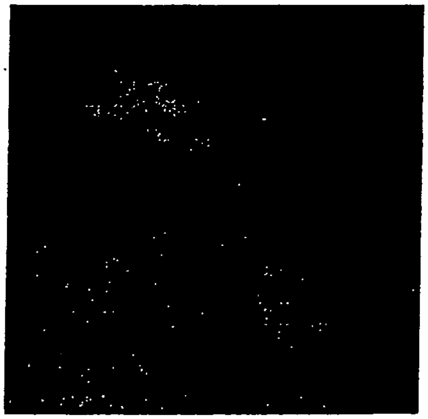

Subcellular localization of agnoprotein in U-87MG cells transfected with pCMV-agnoprotein was also determined. Immunohistochemical examination of transfected U-87MG cells revealed that incubation with pre-immune sera did not detect agnoprotein (FIG. 1B). However, incubation of transfected U-87MG cells with rabbit anti-Agno protein (prepared as described in DeValle L et al. (2002), *J. Nat. Cancer Inst.* 94(4): 267-273, the entire disclosure of which is herein incorporated by reference) showed cytoplasmic perinuclear accumulation of agnoprotein in the cells (FIG. 1C).

To determine the effect of agnoprotein expression on cell cycle progression, U-87MG cells were synchronized and serum stimulated as above. At 4 hrs. after serum stimulation, cells were co-transfected with both pCMV-agnoprotein (which expresses agnoprotein) and pCMV-GFP (which expresses green fluorescent protein, or "GFP"). In parallel, control U-87MG cells were transfected with pCMV-GFP alone. At 23, 28, 47 and 53 hrs. post-stimulation, cells were harvested and the percentages of cells in G1, S, and G2/M were determined by flow cytometry as described above. The time points measured encompassed one complete round of progression through the cell cycle. Cells that expressed GFP were "gated" on the FACS, and the DNA profile of GFP-positive cells from the pCMV-agnoprotein/pCMV-GFP group was compared to that of the control cells transfected with only pCMV-GFP. The results are presented below in Table 4.

TABLE 4

Cell Cycle Progression of U-87MG Cells Expressing GFP or GFP-Agnoprotein

| Hrs. Post Serum | Control (% GFP Cells) | | | Experimental (% GFP + Agno Cells) | | |
|---|---|---|---|---|---|---|
| Induction | G1 | S | G2/M | G1 | S | G2/M |
| 23 | 67 | 17 | 15 | 27 | 21 | 51 |
| 28 | 29 | 17 | 53 | 28 | 18 | 53 |
| 47 | 67 | 13 | 19 | 66 | 14 | 18 |
| 53 | 32 | 15 | 52 | 62 | 12 | 25 |

For the pCMV-GFP control cell group, nearly 67% of the cells were found at the G1 stage and only 15% accumulated at the G2/M stage at 23 hrs. after serum stimulation. These values had significantly changed by 28 hrs. post-stimulation, as only 29% of the cells were found in the G1 phase and more than 53% of the cells had progressed to the G2/M phase. At 47 hrs. post-serum stimulation, 67% of the cells were again found at the G1 stage, and only a minor fraction of the cells (19%) were detected at G2/M. As time progressed, more cells departed from the G1 phase and accumulated in G2/M.

In contrast to the control cells, the majority of pCMV-agnoprotein/pCMV-GFP cells (51%) were found at the G2/M phase and only 27% of the cells were detected at G1 stage at 23 hrs. post-stimulation. At 28 hours post-stimulation, 53% of the cells remained at the G2/M stage. At 47 hrs. post-stimulation, the majority of cells (66%) were found at the G1 stage with only a small population of the cells (18%) detected at G2/M. The population of the cells shifted slightly from G1 to G2/M at 53 h post-stimulation, as 62% and 25% of the cells were detected at G1 and G2/M, respectively.

Without wishing to be bound by any theory, from these data it appears that agnoprotein expression prolongs the progression of cells throughout the cell cycle by stalling cells at the G2/M and G1 stages. This is supported by the observation that, at the earlier hours after serum stimulation (i.e., 4, 12 and 20 hrs.), the population of control and agnoprotein-producing cells which were found at each stage of the cell cycle was virtually identical to those seen at 23 h post-induction.

Example 2

Suppression of Cell Proliferation and Deregulation of the Cell Cycle by Agnoprotein Stable NIH 3T3 cell lines that constitutively express agnoprotein were produced using pYFP-agnoprotein, which is a plasmid containing sequences encoding the agnoprotein fused with the mutant variant of GFP called "yellow fluorescent protein" or "YFP". Examination of YFP-agnoprotein production in the stably transfected NIH 3T3 cell lines showed expression of a fusion protein which appropriately localized in the cytoplasmic perinuclear membrane of the cells. Control cells transfected with pEYFP-N1 (expressing YFP alone) showed no evidence for cellular compartmentalization of YFP.

Figure 2A:
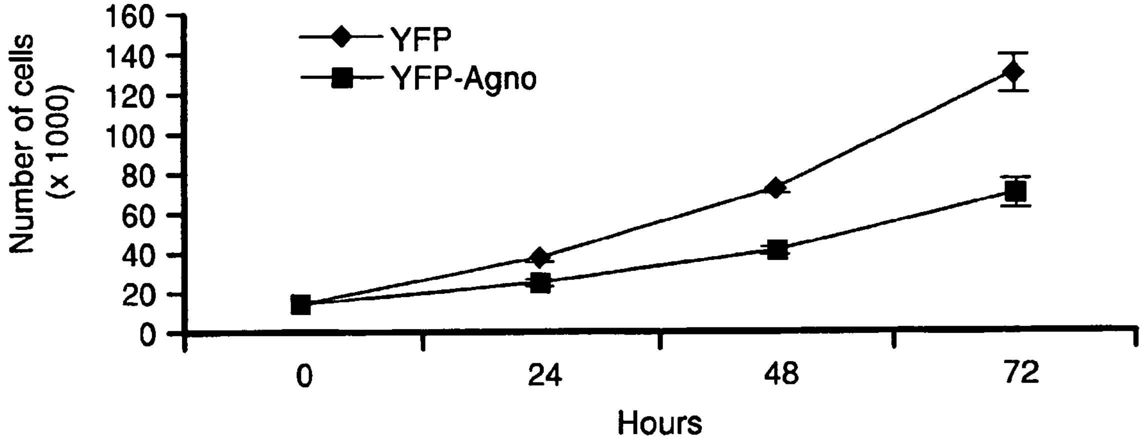
FIG. 2A is a plot comparing proliferation of NIH 3T3 cells in the absence and presence of agnoprotein expression. Four independent samples were tested after 24, 48, and 72 hours for cell proliferation by direct counting of the total number of cells. All error is represented in SEM.

The growth rate of NIH 3T3 cell lines stably expressing either YFP-agnoprotein or YFP alone was examined as follows. An equal number of either cell type was seeded at 20,000 cells/35 mm plate in DMEM plus 10% fetal calf serum. Four independent samples were tested after 24, 48, and 72 hours for cell proliferation by direct counting of the total number of cells, and the experiments were repeated in various stable cell lines to ensure the reproducibility in various clones. FIG. 2A shows an approximately 50% decrease in the number of agnoprotein-producing cells compared to that seen in the control cells.

Figure 2B:
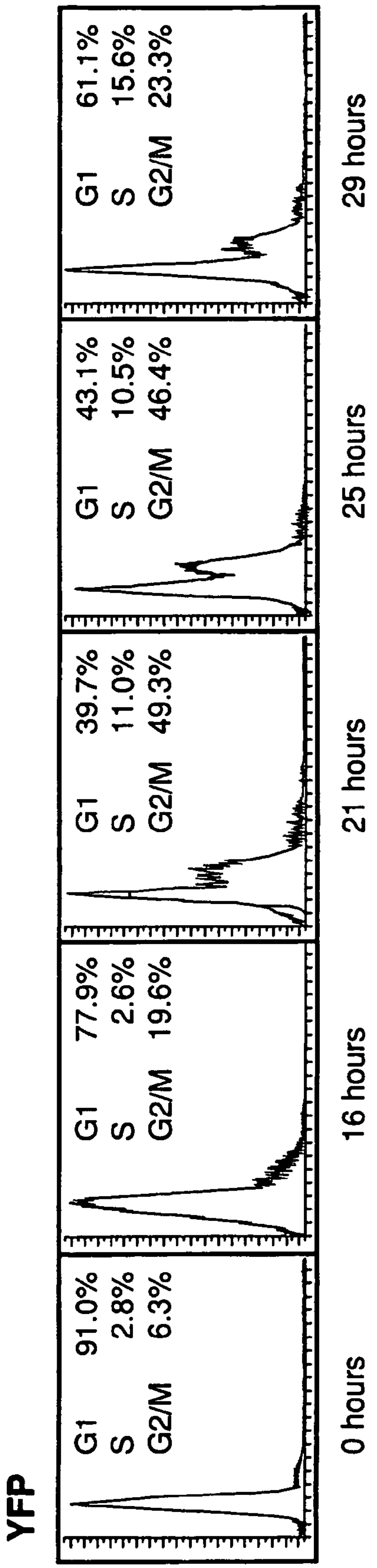
FIGS. 2B and 2C are, respectively, fluorescence-activated cell sorting (FACS) analyses of NIH 3T3 cells stably expressing YFP or YFP-agnoprotein at 0, 16, 21, 25 and 29 hours after serum stimulation. The percentage of cells in G1, S, and G2/M is indicated for each time point. Histograms are representative of three experiments and the average values are presented.

Results from FACS analysis of YFP-producing (control) NIH 3T3 cells revealed that these cells progress abnormally through the cell cycle. At 0 hrs. post serum stimulation, greater than 90% of the YFP-producing cells were found at the G1 phase (FIG. 2B). As time progressed, the cells began to enter the S phase and accumulated at G2/M. By 21 hours post-serum stimulation, only 39% of the cells remained at the G1 and greater than 49% of the cells were found at G2/M. At 25 hrs. post-induction, the cells again appeared to depart from G2/M and accumulate at the G1 phase. At 29 hrs. post-stimulation, nearly 61% of cells were found at the G1 and only 23% were detected at G2/M.

Figure 2C:
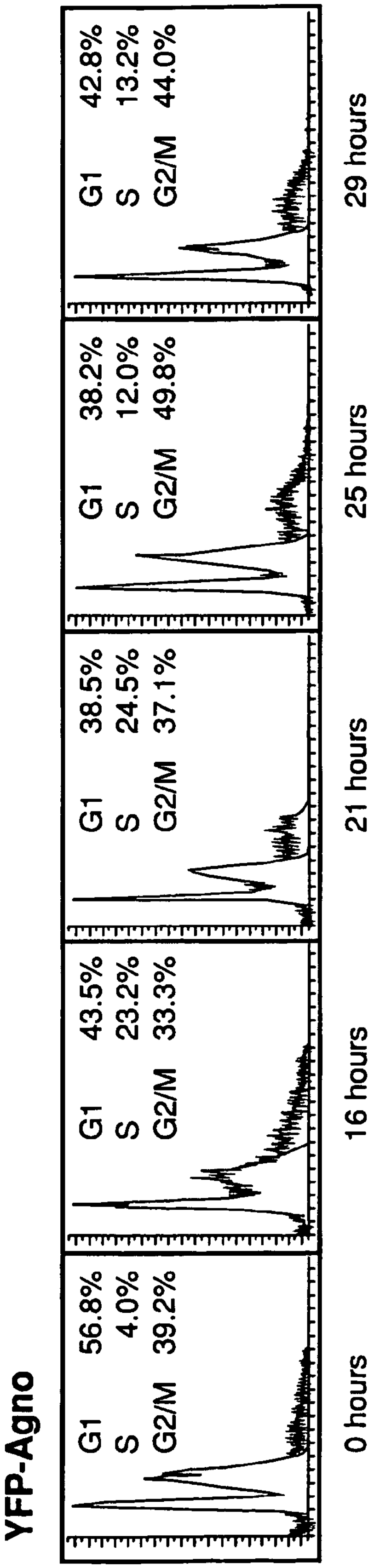

As shown in FIG. 2C, the agnoprotein-producing NIH 3T3 cells exhibited a different pattern of progression through the cell cycle than the control cells. More agnoprotein-producing cells were detected at the G2/M (39.2%) than the control (6.3%) at 0 hrs. post-serum stimulation, and 50% of the agnoprotein-producing cells were found at the G1 stage at this time point. The number of cells at the G1 stage was modestly decreased at 16 and 21 hrs. post-stimulation, and a substantial level of cells were detected at the G2/M phase. Further, a higher number of agnoprotein-producing cells was found at the S phase as compared to control cells. At the later times post-stimulation (i.e., 25 and 29 hrs.), the number of agnoprotein-producing cells at G2/M remained at high levels.

Without wishing to be bound by any theory, these data indicate that expression of agnoprotein deregulates cell cycle progression at various stages, most noticeably by affecting cell departure from G1 to S phase, from S to G2/M, and by inducing an unusual accumulation of cells at G2/M.

Example 3

Expression of Cyclins A and B and their Kinase Activity in Cells Producing Agnoprotein The level of expression and activity of proteins involved in the control of the cell cycle was examined in NIH 3T3 cells expressing agnoprotein. The levels of cyclin D, cdk4, cdk6, cyclin E and cdk2 levels were comparable in synchronized NIH 3T3 cells expressing YFP (control) and NIH 3T3 cells expressing YFP-agnoprotein prepared as above. Since cyclin A/cdc2 and cyclin B/cdc2 provide the major kinase activity during G2/M, the stage which appears to be affected by agnoprotein, the effect of agnoprotein on cyclin A and cyclin B expression was also examined.

Cyclin A—Cyclin A production was evaluated by Western blot analysis of protein extracts from synchronized NIH 3T3 cells expressing YFP (control) or YFP-agnoprotein prepared as above, at 0, 4, 16, 21 and 29 hours after serum stimulation.

Figure 3A:
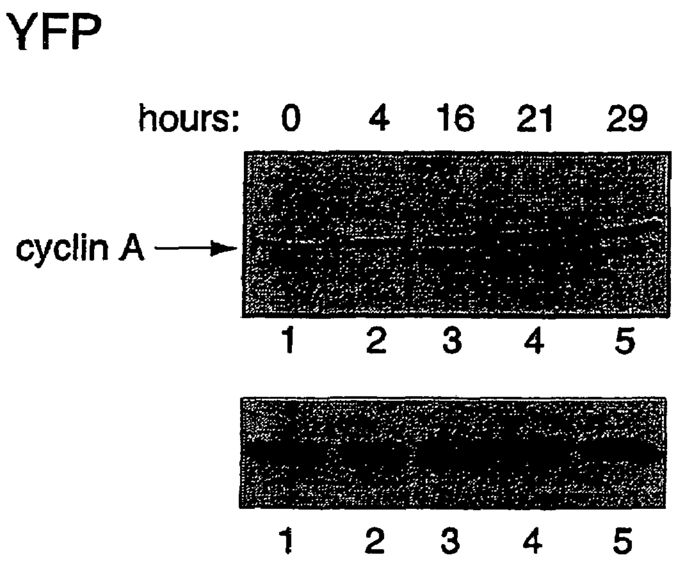
FIGS. 3A and 3B are, respectively, Western blot analyses of cyclin A expression in synchronized NIH 3T3 cells expressing YFP or YFP-agnoprotein at 0, 4, 16, 21 and 29 hours after serum stimulation. 50 μg total protein extract was analyzed for each cell type. As a control for protein loading in the gels, the levels of Grb2 are shown in the bottom panels.
Figure 3B:
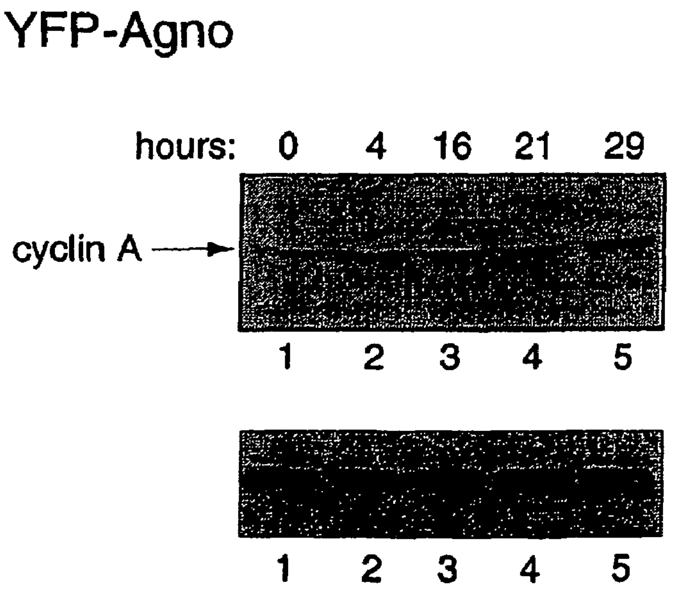

Rabbit anti-cyclin A (C-19; Santa Cruz Biotechnology, Inc., Santa Cruz, Calif.) was used to probe the blot. FIGS. 3A and 3B show a comparable level of cyclin A was expressed in the control and agnoprotein-producing cells. The level of the "housekeeping" protein Grb2 was determined and used a s control for equal protein loading in the gel (see lower panels of FIGS. 3A and 3B).

Figure 3C:
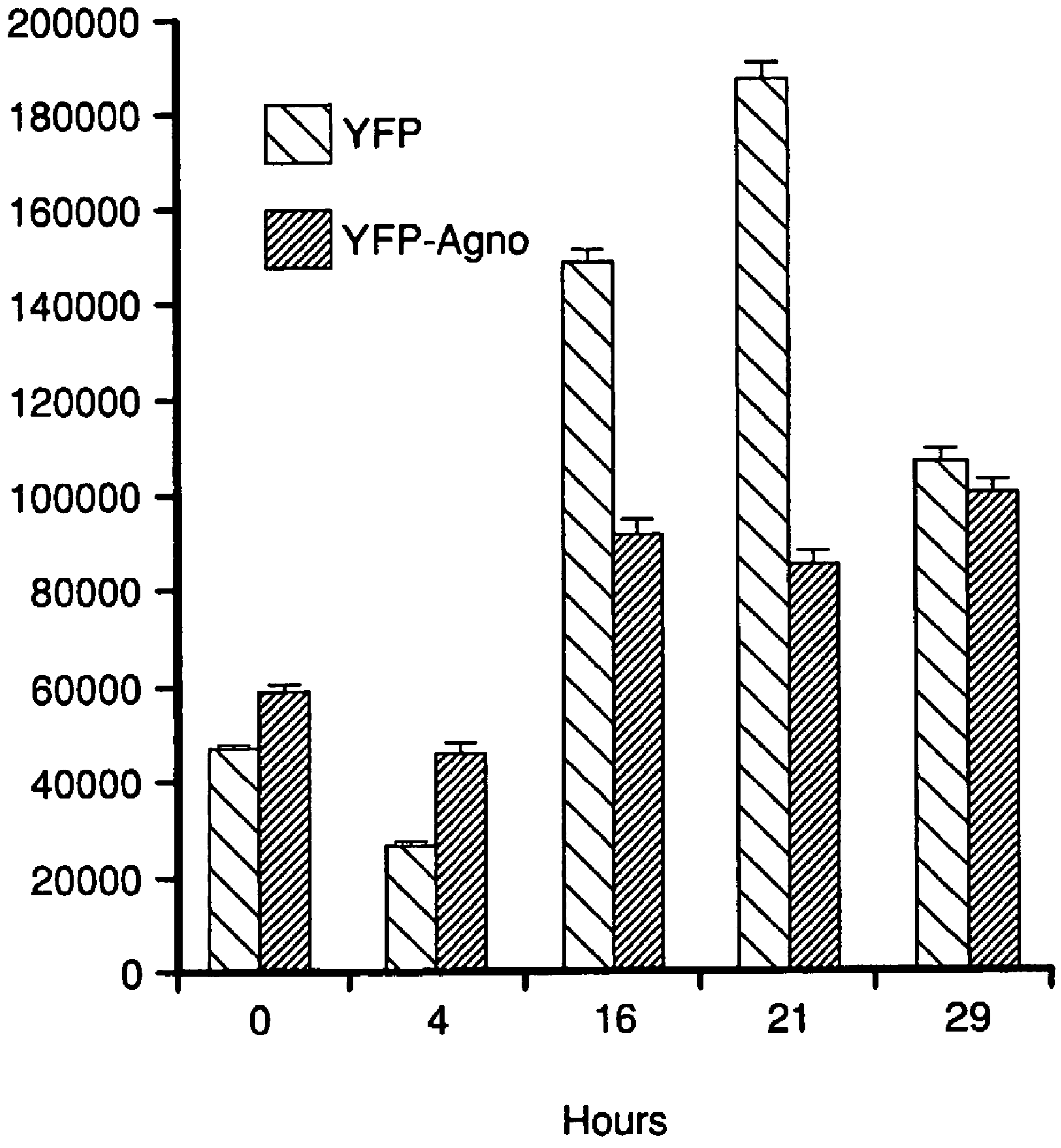
FIG. 3C is a plot showing associated kinase activity of cyclin A in 220 μg of protein extracted from YFP and YFP-agnoprotein producing NIH 3T3 cells at 0, 4, 16, 21 and 29 hours after serum stimulation. Kinase activity is expressed as counts-per-minute (cpm) on the Y axis, and the time after serum stimulation is given in hours on the X axis. The kinase assay was repeated two times for each sample, giving an interassay standard deviation within 10% after normalization for protein amount.

The associated kinase activity of the cyclin A immunocomplex was evaluated by H1 kinase assay. FIG. 3C shows a 35% and 55% decrease in cyclin A-associated kinase activity from agnoprotein-producing protein extracts vs. control cell protein extracts at 16 and 21 hours after serum induction, respectively. Cyclin A-associated kinase activity declined at 29 hrs. after serum induction in the control cells, but not in the agnoprotein producing cells (FIG. 3C).

Figure 4A:
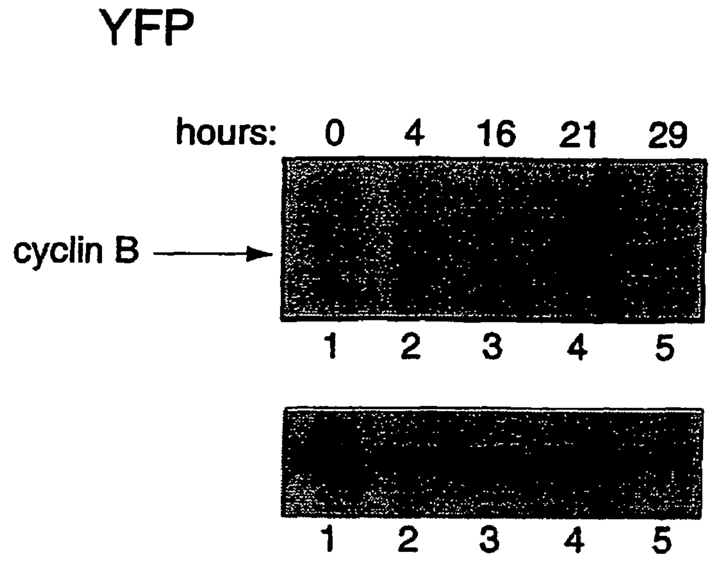
FIGS. 4A and 4B are, respectively, Western blot analyses of cyclin B expression in synchronized NIH 3T3 cells expressing YFP or YFP-agnoprotein at 0, 4, 16, 21 and 29 hours after serum stimulation. 50 μg total protein extract was analyzed for each cell type. As a control for protein loading in the gels, the levels of Grb2 are shown in the bottom panels.
Figure 4B:
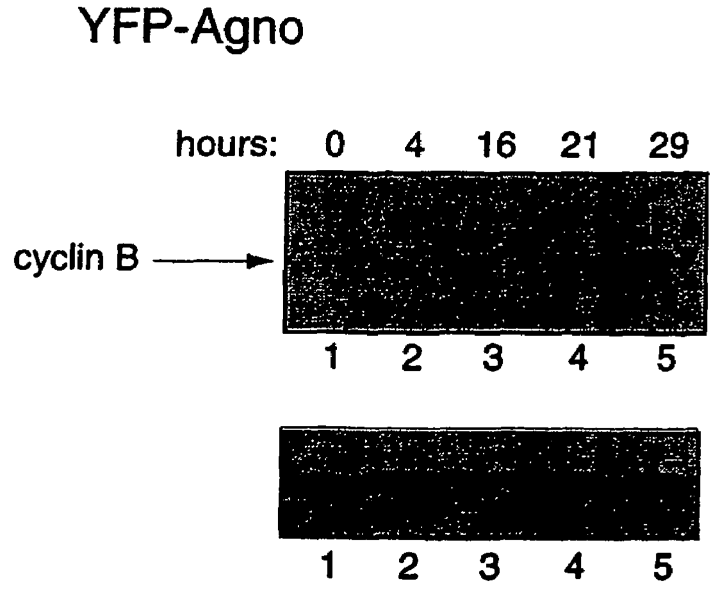

Cyclin B—Cyclin B levels in synchronized NIH 3T3 cells expressing YFP (control) or YFP-agnoprotein were examined by Western blot analysis at 0, 4, 16, 21 and 29 hrs. after serum stimulation. Mouse anti-cyclin B1 (clone GNS1; Santa Cruz Biotechnology, Inc., Santa Cruz, Calif.) was used to probe the blot. Both control and agnoprotein-producing cells showed a noticeable increase in the level of cyclin B at 21 hrs. post-stimulation in (FIGS. 4A and 4B). However, the level of cyclin B in agnoprotein-producing cells was slightly decreased overall vs. control, particularly at 21 hrs. post-stimulation (see FIGS. 4A and 4B, lane 4). This difference was not a general event, as the levels of other cellular proteins, including cyclin A (see FIG. 3) and "housekeeping" proteins such as Grb2 (see lower panels of FIGS. 4A and 4B), remained unchanged in agnoprotein-producing cells relative to control cells.

Figure 4C:
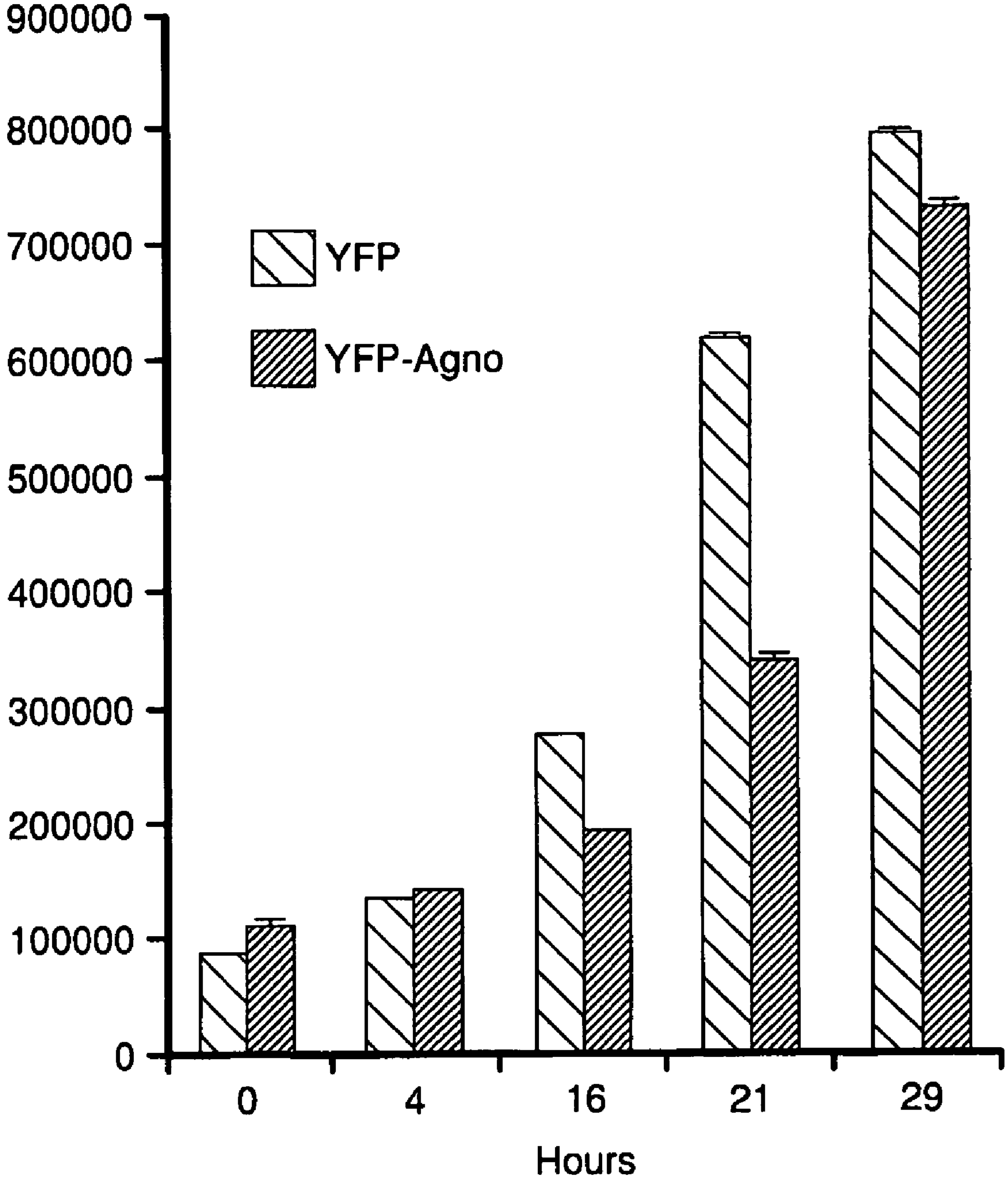
FIG. 4C is a plot showing associated kinase activity of cyclin B in 220 μg of protein extracted from YFP and YFP-agnoprotein producing NIH 3T3 cells at 0, 4, 16, 21 and 29 hours after serum stimulation. Kinase activity is expressed as counts-per-minute (cpm) on the Y axis, and the time after serum stimulation is given in hours on the X axis. Kinase activity is expressed as the average of two experiments after normalization for protein levels.

The associated kinase activity of the cyclin B immunocomplex was evaluated by H1 kinase assay. FIG. 4C shows showed a decrease in cyclin B-associated kinase activity in agnoprotein-producing cells vs. control cells from 16 hrs. post-serum stimulation, including a 40% reduction in kinase activity at 21 hrs. post-serum stimulation.

Example 4

Expression of Tumor Suppressor Proteins in NIH 3T3 Cells Expressing Agnoprotein The levels of cell cycle inhibitor proteins p27, p21 and p53 were examined by Western blot analysis on protein extracts from NIH 3T3 cells expressing YFP (control) or YFP-agnoprotein. The blots were probed with anti-p27 and anti-β-actin (Santa Cruz Biotechnology, Inc.); rabbit anti-p21/WAF-1 (Ab-5) and mouse anti-p53 (Ab-1) (Oncogene Science, Boston, Mass.).

Figure 5A:
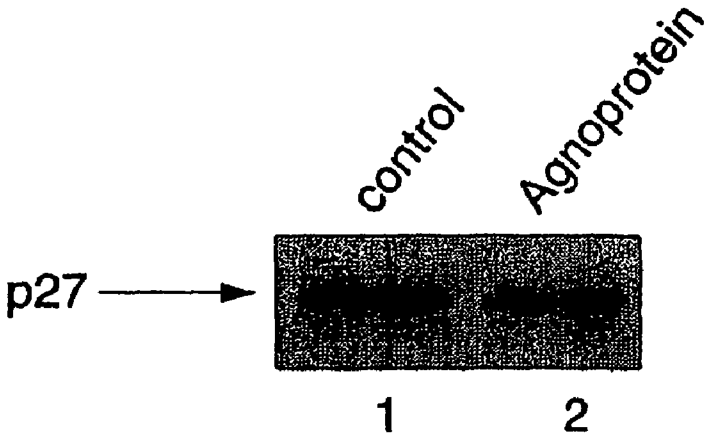
FIGS. 5A-C are, respectively, Western blot analyses of approximately 50 μg of total protein extracted from NIH 3T3 ("control") and NIH 3T3-agnoprotein ("Agnoprotein") producing cell lines using antibodies that recognize p27, p21 and β-actin.
Figure 5B:
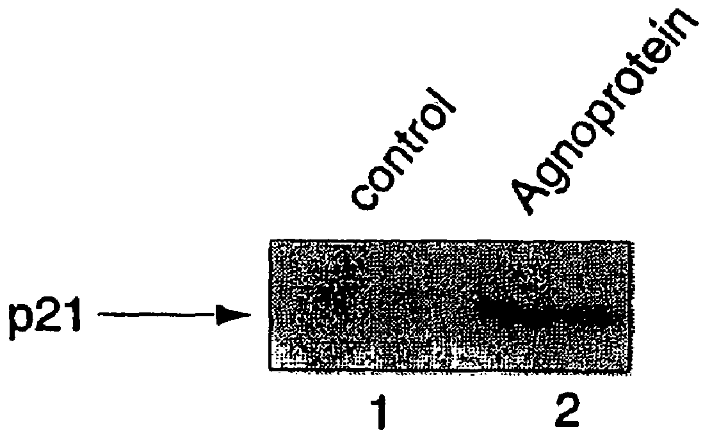
Figure 5C:
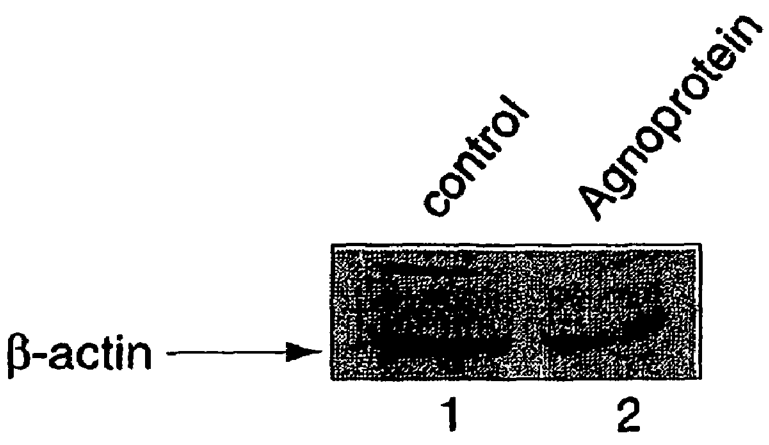

FIGS. 5A showed no significant differences in the levels of p27 in the control and agnoprotein-expressing cells. However, the level of p21 was increased in agnoprotein-producing cells as compared to control (FIG. 5B). Again, the level of expression of other cellular proteins such as β-actin remained unchanged in the control and agnoprotein-producing cells (FIG. 5C).

The ability of agnoprotein to enhance the transcriptional activity of the p21 promoter was also evaluated. Saos-2 cells (which lack endogenous p53) were transfected with plasmid p21-luciferase. Plasmid p21-luciferase has a p21 promoter linked to a luciferase reporter gene, and activation of the p21 promoter causes an increase in luciferase activity.

Figure 5D:
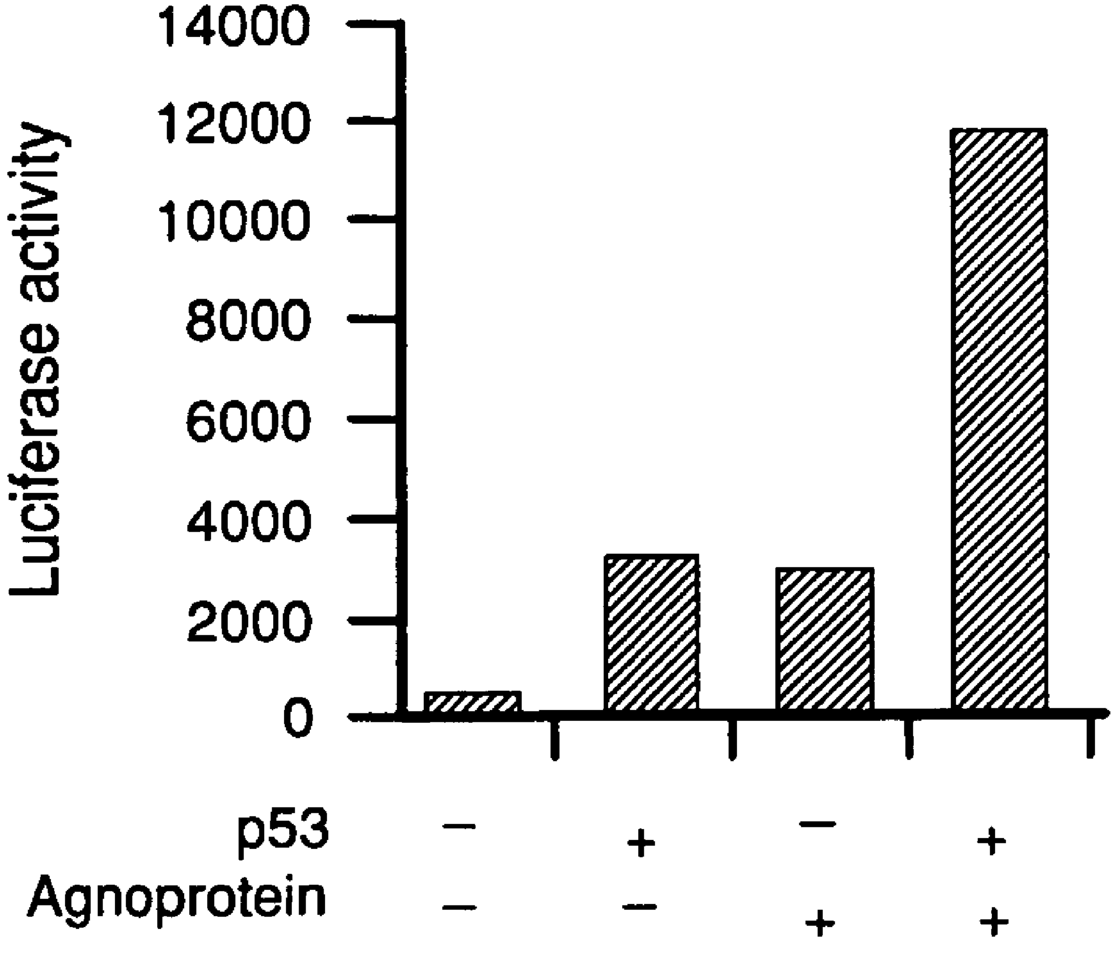
FIG. 5D is plot of luciferase activity in Saos-2 cells transfected with a p21-luciferase reporter gene alone, or with plasmids expressing p53 ("p53 +/−") or agnoprotein ("Agnoprotein+/−").

Saos-2 cells containing the p21-luciferase plasmid were then transfected with either pCMV-Agnoprotein or a plasmid expressing p53, or both. As shown in FIG. 5D, transcriptional activity of the p21 promoter was increased upon expression of either agnoprotein or p53 in transfected Saos-2 cells containing the p21-luciferase plasmid. Co-expression of both agnoprotein and p53 caused a synergistic elevation of p21 promoter activity. These results indicate that agnoprotein increases the level of p21 promoter-driven transcription, and the cooperativity of agnoprotein with p53 can further elevate expression of p21 in cells.

Activation of p21 in agnoprotein-producing cells, which are deregulated in G1 as well as G2/M, is noteworthy in light of recent reports demonstrating that p21 contributes to the regulation of the G2/M transition (see Niculescu A B, III et al. (1998) *Mol. Cell. Biol.* 18, 629-643). Without wishing to be bound by any theory, the activation of p21 in agnoprotein-producing cells may contribute to the de-regulation of G1 as well as G2/M, which leads to growth arrest.

Figure 6A:
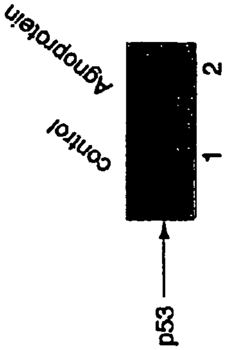
FIG. 6A is a Western blot analysis of 50 μg protein extracted from control and agnoprotein-producing NIH 3T3 cells using anti-p53 antibody

There were also no significant differences in p53 levels of control vs. agnoprotein-producing cells (FIG. 6A). p53 is an upstream regulator of p21. Without wishing to be bound by any theory, these data suggest that a p53 independent pathway may up-regulate expression of p21 in agnoprotein-producing cells.

Example 5

Association of Agnoprotein with p53

Figure 6B:
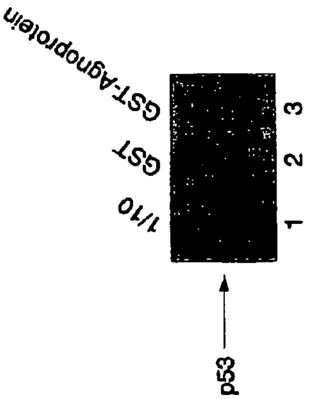
FIG. 6B is an autoradiograph of agnoprotein that was immobilized on glutathione-Sepharose beads, incubated with in vitro translated [$^{35}$S]-methionine-labeled p53 and resolved by SDS-PAGE. One-tenth of the input p53 used in each reaction was loaded as a migrating control in lane 1.
Figure 6C:
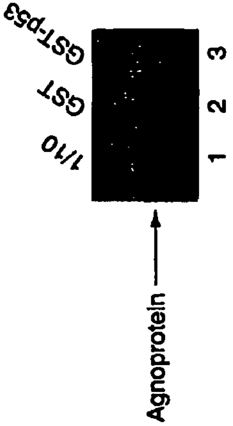
FIG. 6C is an autoradiograph of p53 fused to GST beads mixed with in vitro translated [$^{35}$S]-labeled agnoprotein and resolved by SDS-PAGE. One-tenth of the of the input from the in vitro translation reaction was loaded as a migrating control in lane 1.
Figure 6D:
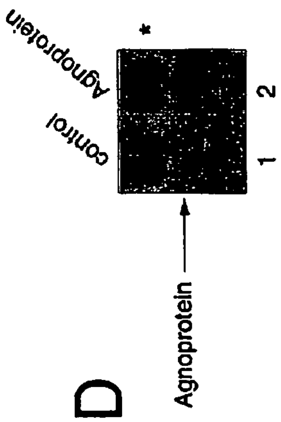
FIG. 6D is a Western blot analysis of immunoprecipitates from 150 μg protein extracted from control NIH 3T3 and agnoprotein-producing NIH 3T3 cells. The position of the fusion agnoprotein is shown by an arrow. The asterisk indicates a non-specific band seen in both control and experimental cell extracts.

As p53 activity can be regulated through association with other proteins, the ability of agnoprotein to interact with p53 was examined. Protein extracts from NIH 3T3 cells expressing YFP (control) or YFP-agnoprotein were immunoprecipitated with p53-specific antibody pAb 421. Immunoprecipitated proteins were resolved by SDS-PAGE and analyzed by Western blot using a rabbit anti-Agno protein as described in DeValle L et al. (2002), supra. As shown in FIG. 6D, a distinct agnoprotein-positive band was observed for the extracts from agnoprotein-producing cells, which was absent from the control cell extracts. These data suggest that p53 and agnoprotein are associated in the protein extract.

To verify the interaction of agnoprotein with p53, in vitro synthesized [$^{35}$S]-labeled p53 was incubated with GST alone or with a GST-agnoprotein fusion protein. After 1 hr. incubation at 4° C., the complexes bound to resin were precipitated and washed with binding buffer as described in Safak M et al. (2001), supra. Bound proteins were diluted by boiling in Laemmli buffer, resolved by SDS-PAGE, and detected by autoradiography. As shown in FIG. 6B, the 53 kDa [$^{35}$S]-labeled p53 was retained by the GST-agnoprotein, but not by GST alone.

In the reciprocal experiment, in vitro synthesized, [$^{35}$S]-labeled agnoprotein was incubated with GST or GST-p53, and the bound proteins were resolved by SDS-PAGE followed by autoradiography. As shown in FIG. 6C, a band corresponding to agnoprotein was detected in GST-p53 lane, but not in the GST lane.

Figure 6E:
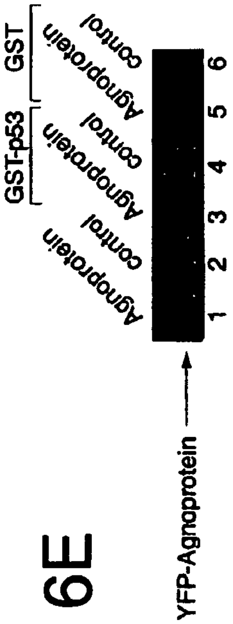
FIG. 6E is a Western blot analysis of immnunoprecipitates from approximately 250 μg protein extracted from control cells expressing YFP or cells expressing GFP-Agnoprotein were analyzed by GST pull-down assay using GST or GST-p53 as indicated. Lanes 1 and 2 represent an analysis of 50 μg protein extract from each cell type which was used in the binding experiment. The arrow indicates the position of YFP-Agnoprotein.

In a further approach to demonstrate the interaction of agnoprotein and p53, protein extracts from YFP-producing NIH-3T3 cells and control NIH-3T3 cells expressing only YFP were mixed with GST-p53 or GST alone, and the bound proteins were analyzed by Western blot using anti-agnoprotein antibody. As shown in FIG. 6E, a band corresponding the YFP-agnoprotein was observed in GST-p53, but not on GST alone fractions.

To determine the regions of agnoprotein which associates with p53, a GST pull-down assay using fusion proteins in which various regions of agnoprotein were fused to GST was conducted. The agnoprotein fusion protein used in the pull down assay were (with numbers indicating the number of amino acids in the N- to C-terminal direction on the JCV agnoprotein): GST-Agno 1-71; GST-Agno 1-54; GST-Agno 1-36; GST-Agno 36-71; GST-Agno 55-71; GST-Agno 18-54; and GST-Agno 18-71.

Figure 6F:
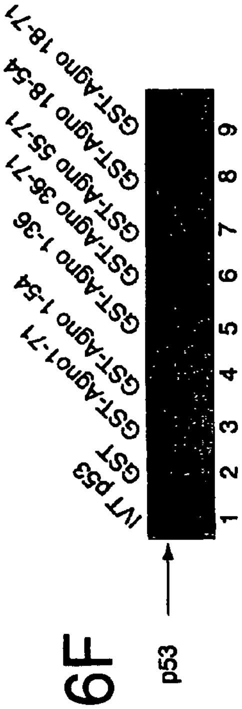
FIG. 6F is an autoradiograph of in vitro [$^{35}$S]-methionine-labeled p53 protein analyzed by GST pull-down assay using various regions of the agnoprotein as indicated, which were fused to GST. The position of the labeled p53 is indicated by the arrow.

As shown in FIG. 6F, the N-terminal region of agnoprotein from amino acids 1 to 36 is sufficient for binding to p53. This region of agnoprotein encompasses a helix-loop-helix structure which has 63% homology with the SV40 agnoprotein.

Thus, it is evident that agnoprotein is able to interact with p53. Without wishing to be bound by any theory, the interaction of agnoprotein and p53 may affect other events involved in the control of cell cycle progression (such as expression of downstream targets of p53) and contribute to the inhibition of cell growth effected by agnoprotein.

All documents referred to herein are incorporated by reference. While the present invention has been described in connection with the preferred embodiments and the various figures, it is to be understood that other similar embodiments may be used or modifications and additions made to the described embodiments for performing the same function of the present invention without deviating therefrom. Therefore, the present invention should not be limited to any single embodiment, but rather should be construed in breadth and scope in accordance with the recitation of the appended claims.

I claim:

1. A method of inhibiting cell growth comprising introducing into a cell an effective amount of (i) an agnoprotein comprising the amino acid sequence of SEQ ID NO: 1, (ii) one or more biologically active fragments of agnoprotein, wherein said one or more fragments comprise amino acid residues 1-36 of SEQ ID NO: 1, or (iii) one or more derivatives of agnoprotein, wherein the amino acid sequence of said one or more derivatives have at least about 83% sequence identity to SEQ ID NO: 1, and wherein said one or more derivatives have cell growth inhibitory activity, such that growth of the cell is inhibited.

2. The method of claim 1, wherein the cells are abnormally proliferating cells.

3. The method of claim 2, wherein the abnormally proliferating cells are cancer cells.

4. The method of claim 2, wherein the abnormally proliferating cells are fibroblasts.

5. The method of claim 1 wherein the agnoprotein comprises a JCV agnoprotein.

6. The method of claim 5, wherein the JCV agnoprotein is selected from the group consisting of SEQ ID NO: 1; SEQ ID NO: 3; SEQ ID NO: 4; SEQ ID NO: 5; SEQ ID NO: 6; and SEQ ID NO: 7.

7. The method of claim 1 wherein the agnoprotein comprises a protein having the amino acid sequence:

8. The method of claim 1 wherein the agnoprotein comprises BK virus agnoprotein or SV40 agnoprotein.

9. The method of claim 8, wherein the BK virus agnoprotein is selected from the group consisting of SEQ ID NO: 14 and SEQ ID NO: 15.

10. The method of claim 8, wherein the SV4O agnoprotein comprises SEQ ID NO: 17.

11. The method of claim 1, wherein the agnoprotein derivative comprises SEQ ID NO: 22.

12. A method of treating a subject having a glioblastoma, comprising administering to the subject an effective amount of (i) an agnoprotein comprising the amino acid sequence of SEQ ID NO: 1, (ii) one or more biologically active fragments of agnoprotein, wherein said one or more fragments comprise amino acid residues 1-36 of SEQ ID NO: 1, or (iii) one or more derivatives of agnoprotein, wherein the amino acid sequence of said one or more derivatives have at least about 83% sequence identity to SEQ ID NO: 1, and wherein said one or more derivatives have cell growth inhibitory activity, such that growth of cells deriving from the glioblastoma is inhibited.

13. The method of claim 12, wherein the one or more agnoproteins, or the one or more biologically active fragments or derivatives of agnoprotein, is administered by direct injection into a tissue comprising the cells deriving from a glioblastoma.

M-V-L-R-Q-L-S-R-K-A-S-V-K-V-S-K-T-W-S-G-T-K-K-R-A-Q-R-I-L-I-F-L-L-E-F-L- (SEQ ID NO: 13)
L-D-F-C-T-G-E-D-$X_1$-V-D-G-K-K-R-Q-$X_2$-H-$X_3$-$X_4$-$X_5$-$X_6$-$X_7$-$X_8$-$X_9$-$X_{10}$-$X_{11}$-A-L-P-
E-P-K-A-$X_{12}$, wherein $X_1$ is serine or arginine;

$X_2$ is lysine or arginine;

$X_3$ is serine or arginine;

$X_4$ is glycine or no amino acid;

$X_5$ is leucine or no amino acid;

$X_6$ is threonine or no amino acid;

$X_7$ is glutamine, glutamic acid, or no amino acid;

$X_8$ is glutamine or no amino acid;

$X_9$ is threonine, arginine, lysine or no amino acid;

$X_{10}$ is tyrosine or no amino acid; $X_{11}$ is serine or glycine; and $X_{12}$ is threonine or lysine.

14. The method of claim 12, wherein the agnoprotein comprises a JCV agnoprotein.

15. The method of claim 14, wherein the JCV agnoprotein is selected from the group consisting of SEQ ID NO: 1; SEQ ID NO: 3; SEQ ID NO: 4; SEQ ID NO: 5; SEQ ID NO: 6 and SEQ ID NO: 7.

16. The method of claim 12 wherein the agnoprotein comprises a protein having the amino acid sequence:

M-V-L-R-Q-L-S-R-K-A-S-V-K-V-S-K-T-W-S-G-T-K-K-R-A-Q-R-I-L-I-F-L-L-E-F-L-L-D-F-C-T-G-E-D-$X_1$-V-D-G-K-K-R-Q-$X_2$-H-$X_3$-$X_4$-$X_5$-$X_6$-$X_7$-$X_8$-$X_9$-$X_{10}$-$X_{11}$-A-L-P-E-P-K-A-$X_{12}$, (SEQ ID NO: 13)

wherein $X_1$ is serine or arginine;

$X_2$ is lysine or arginine;

$X_3$ is serine or arginine;

$X_4$ is glycine or no amino acid;

$X_5$ is leucine or no amino acid;

$X_6$ is threonine or no amino acid;

$X_7$ is glutamine, glutamic acid, or no amino acid;

$X_8$ is glutamine or no amino acid;

$X_9$ is threonine, arginine, lysine or no amino acid;

$X_{10}$ is tyrosine or no amino acid;

$X_{11}$ is serine or glycine; and $X_{12}$ is threonine or lysine.

17. The method of claim 12 wherein the agnoprotein comprises a BK virus agnoprotein or SV40 agnoprotein.

18. The method of claim 17, wherein the BK virus agnoprotein is selected from the group consisting of SEQ ID NO: 14 and SEQ ID NO: 15.

19. The method of claim 17, wherein the SV40 agnoprotein comprises SEQ ID NO: 17.

20. The method of claim 12, wherein the agnoprotein derivative comprises SEQ ID NO: 22.

* * * * *

UNITED STATES PATENT AND TRADEMARK OFFICE

CERTIFICATE OF CORRECTION

PATENT NO. : 7,612,039 B2
APPLICATION NO. : 10/517710
DATED : November 3, 2009
INVENTOR(S) : Khalili It is certified that error appears in the above-identified patent and that said Letters Patent is hereby corrected as shown below:

On the cover page,

[*] Notice: Subject to any disclaimer, the term of this patent is extended or adjusted under 35 USC 154(b) by 221 days.

Delete the phrase "by 221 days" and insert -- by 426 days --

Signed and Sealed this

Tenth Day of August, 2010

David J. Kappos

*Director of the United States Patent and Trademark Office*

UNITED STATES PATENT AND TRADEMARK OFFICE

CERTIFICATE OF CORRECTION

PATENT NO. : 7,612,039 B2
APPLICATION NO. : 10/517710
DATED : November 3, 2009
INVENTOR(S) : Kamel Khalili It is certified that error appears in the above-identified patent and that said Letters Patent is hereby corrected as shown below:

Column 1, lines 6-8, cancel the text and insert the following:

--This invention was made with government support under grants P01 NS30916 and P01 NS36466 awarded by the National Institutes of Health. The government has certain rights in the invention.--

Signed and Sealed this
Eleventh Day of October, 2011

David J. Kappos
*Director of the United States Patent and Trademark Office*

```
                        SEQUENCE LISTING

<160> NUMBER OF SEQ ID NOS: 28

<210> SEQ ID NO 1
<211> LENGTH: 71
<212> TYPE: PRT
<213> ORGANISM: JC virus

<400> SEQUENCE: 1

Met Val Leu Arg Gln Leu Ser Arg Lys Ala Ser Val Lys Val Ser Lys
 1               5                  10                  15

Thr Trp Ser Gly Thr Lys Lys Arg Ala Gln Arg Ile Leu Ile Phe Leu
            20                  25                  30

Leu Glu Phe Leu Leu Asp Phe Cys Thr Gly Glu Asp Ser Val Asp Gly
        35                  40                  45

Lys Lys Arg Gln Arg His Ser Gly Leu Thr Glu Gln Thr Tyr Ser Ala
    50                  55                  60

Leu Pro Glu Pro Lys Ala Thr
65                  70


<210> SEQ ID NO 2
<211> LENGTH: 216
<212> TYPE: DNA
<213> ORGANISM: JC virus

<400> SEQUENCE: 2

atggttcttc gccagctgtc acgtaaggct tctgtgaaag ttagtaaaac ctggagtgga      60

actaaaaaaa gagctcaaag gattttaatt tttttgttag aatttttgct ggacttttgc     120

acaggtgaag acagtgtaga cgggaaaaaa agacagagac acagtggttt gactgagcag     180

acatacagtg ctttgcctga accaaaagct acatag                               216


<210> SEQ ID NO 3
<211> LENGTH: 71
<212> TYPE: PRT
<213> ORGANISM: JC virus

<400> SEQUENCE: 3

Met Val Leu Arg Gln Leu Ser Arg Lys Ala Ser Val Lys Val Ser Lys
 1               5                  10                  15

Thr Trp Ser Gly Thr Lys Lys Arg Ala Gln Arg Ile Leu Ile Phe Leu
            20                  25                  30

Leu Glu Phe Leu Leu Asp Phe Cys Thr Gly Glu Asp Ser Val Asp Gly
        35                  40                  45

Lys Lys Arg Gln Lys His Ser Gly Leu Thr Glu Gln Thr Tyr Ser Ala
    50                  55                  60
```

```
Leu Pro Glu Pro Lys Ala Thr
65                  70


<210> SEQ ID NO 4
<211> LENGTH: 71
<212> TYPE: PRT
<213> ORGANISM: JC virus

<400> SEQUENCE: 4

Met Val Leu Arg Gln Leu Ser Arg Lys Ala Ser Val Lys Val Ser Lys
 1               5                  10                  15

Thr Trp Ser Gly Thr Lys Lys Arg Ala Gln Arg Ile Leu Ile Phe Leu
            20                  25                  30

Leu Glu Phe Leu Leu Asp Phe Cys Thr Gly Glu Asp Ser Val Asp Gly
        35                  40                  45

Lys Lys Arg Gln Arg His Ser Gly Leu Thr Glu Gln Thr Tyr Ser Ala
    50                  55                  60

Leu Pro Glu Pro Lys Ala Thr
65                  70


<210> SEQ ID NO 5
<211> LENGTH: 71
<212> TYPE: PRT
<213> ORGANISM: JC virus

<400> SEQUENCE: 5

Met Val Leu Arg Gln Leu Ser Arg Lys Ala Ser Val Lys Val Ser Lys
 1               5                  10                  15

Thr Trp Ser Gly Thr Lys Lys Arg Ala Gln Arg Ile Leu Ile Phe Leu
            20                  25                  30

Leu Glu Phe Leu Leu Asp Phe Cys Thr Gly Glu Asp Ser Val Asp Gly
        35                  40                  45

Lys Lys Arg Gln Lys His Ser Gly Leu Thr Glu Gln Thr Tyr Ser Ala
    50                  55                  60

Leu Pro Glu Pro Lys Ala Lys
65                  70


<210> SEQ ID NO 6
<211> LENGTH: 71
<212> TYPE: PRT
<213> ORGANISM: JC virus

<400> SEQUENCE: 6

Met Val Leu Arg Gln Leu Ser Arg Lys Ala Ser Val Lys Val Ser Lys
 1               5                  10                  15

Thr Trp Ser Gly Thr Lys Lys Arg Ala Gln Arg Ile Leu Ile Phe Leu
            20                  25                  30

Leu Glu Phe Leu Leu Asp Phe Cys Thr Gly Glu Asp Arg Val Asp Gly
        35                  40                  45

Lys Lys Arg Gln Lys His Ser Gly Leu Thr Glu Gln Thr Tyr Ser Ala
    50                  55                  60

Leu Pro Glu Pro Lys Ala Thr
65                  70


<210> SEQ ID NO 7
<211> LENGTH: 71
<212> TYPE: PRT
<213> ORGANISM: JC virus
```

-continued

<400> SEQUENCE: 7

```
Met Val Leu Arg Gln Leu Ser Arg Lys Ala Ser Val Lys Val Ser Lys
 1               5                  10                  15

Thr Trp Ser Gly Thr Lys Lys Arg Ala Gln Arg Ile Leu Ile Phe Leu
            20                  25                  30

Leu Glu Phe Leu Leu Asp Phe Cys Thr Gly Glu Asp Ser Val Asp Gly
        35                  40                  45

Lys Lys Arg Gln Lys His Arg Gly Leu Thr Glu Gln Thr Tyr Ser Ala
    50                  55                  60

Leu Pro Glu Pro Lys Ala Thr
65                  70
```

<210> SEQ ID NO 8
<211> LENGTH: 216
<212> TYPE: DNA
<213> ORGANISM: JC virus

<400> SEQUENCE: 8

```
atggttcttc gccagctgtc acgtaaggct tctgtgaaag ttagtaaaac ctggagtgga     60

actaaaaaaa gagctcaaag gattttaatt tttttgttag aatttttgct ggatttttgc    120

acaggtgaag acagtgtaga cgggaaaaaa agacagaaac acagtggttt gactgagcag    180

acatacagtg ctttgcctga accaaaagct acatag                              216
```

<210> SEQ ID NO 9
<211> LENGTH: 216
<212> TYPE: DNA
<213> ORGANISM: JC virus

<400> SEQUENCE: 9

```
atggttcttc gccagctgtc acgtaaggct tctgtgaaag ttagtaaaac ctggagtgga     60

actaaaaaaa gagctcaaag gattttaatt tttttgttag aatttttgct ggacttttgc    120

acaggtgaag acagtgtaga cgggaaaaaa agacagagac acagtggttt gactgagcag    180

acatacagtg ctttgcctga accaaaagct acatag                              216
```

<210> SEQ ID NO 10
<211> LENGTH: 216
<212> TYPE: DNA
<213> ORGANISM: JC virus

<400> SEQUENCE: 10

```
atggttcttc gccagctgtc acgtaaggct tctgtgaaag ttagtaaaac ctggagtgga     60

actaaaaaaa gagcccaaag gattttaatt tttttgttag aatttttgct ggatttttgc    120

acaggtgaag acagtgtaga cgggaaaaaa agacagaaac acagtggttt gactgagcag    180

acatacagtg ctttgcctga accaaaagct aaatag                              216
```

<210> SEQ ID NO 11
<211> LENGTH: 216
<212> TYPE: DNA
<213> ORGANISM: JC virus

<400> SEQUENCE: 11

```
atggttcttc gccagctgtc acgtaaggct tctgtgaaag ttagtaaaac ctggagtgga     60

actaaaaaaa gagctcaaag gattttaatt tttttgttag aatttttgct ggacttttgc    120

acaggtgaag acagagtaga cgggaaaaaa agacagaaac acagtggttt gactgagcag    180
```

-continued

```
acatacagtg ctttgcctga accaaaagct acatag                          216


<210> SEQ ID NO 12
<211> LENGTH: 216
<212> TYPE: DNA
<213> ORGANISM: JC virus

<400> SEQUENCE: 12

atggttcttc gccagctgtc acgtaaggct tctgtgaaag ttagtaaaac ctggagtgga     60

actaaaaaaa gagctcaaag gattttaatt tttttgttag aatttttgct ggacttttgc    120

acaggtgaag acagtgtaga cgggaaaaaa agacagaaac acagaggttt gactgagcag    180

acatacagtg ctttgcctga accaaaagct acatag                          216


<210> SEQ ID NO 13
<211> LENGTH: 71
<212> TYPE: PRT
<213> ORGANISM: Artificial Sequence
<220> FEATURE:
<223> OTHER INFORMATION: JCV agnoprotein consensus sequence
<220> FEATURE:
<221> NAME/KEY: VARIANT
<222> LOCATION: 45
<223> OTHER INFORMATION: Xaa=Ser or Arg
<220> FEATURE:
<221> NAME/KEY: VARIANT
<222> LOCATION: 53
<223> OTHER INFORMATION: Xaa=Lys or Arg
<220> FEATURE:
<221> NAME/KEY: VARIANT
<222> LOCATION: 55
<223> OTHER INFORMATION: Xaa=Ser or Arg
<220> FEATURE:
<221> NAME/KEY: VARIANT
<222> LOCATION: 56
<223> OTHER INFORMATION: Xaa=Gly or None
<220> FEATURE:
<221> NAME/KEY: VARIANT
<222> LOCATION: 57
<223> OTHER INFORMATION: Xaa=Leu or None
<220> FEATURE:
<221> NAME/KEY: VARIANT
<222> LOCATION: (58)...(58)
<223> OTHER INFORMATION: Xaa=Thr or None
<220> FEATURE:
<221> NAME/KEY: VARIANT
<222> LOCATION: (59)...(59)
<223> OTHER INFORMATION: Xaa=Glu, Gln or None
<220> FEATURE:
<221> NAME/KEY: VARIANT
<222> LOCATION: (60)...(60)
<223> OTHER INFORMATION: Xaa=Gln or None
<220> FEATURE:
<221> NAME/KEY: VARIANT
<222> LOCATION: (61)...(61)
<223> OTHER INFORMATION: Xaa=Thr, Arg, Lys or None
<220> FEATURE:
<221> NAME/KEY: VARIANT
<222> LOCATION: (62)...(62)
<223> OTHER INFORMATION: Xaa=Tyr or None
<220> FEATURE:
<221> NAME/KEY: VARIANT
<222> LOCATION: (63)...(63)
<223> OTHER INFORMATION: Xaa=Ser or Gly
<220> FEATURE:
<221> NAME/KEY: VARIANT
<222> LOCATION: (71)...(71)
<223> OTHER INFORMATION: Xaa=Thr or Lys

<400> SEQUENCE: 13

Met Val Leu Arg Gln Leu Ser Arg Lys Ala Ser Val Lys Val Ser Lys
 1               5                   10                  15
```

-continued

```
Thr Trp Ser Gly Thr Lys Lys Arg Ala Gln Arg Ile Leu Ile Phe Leu
            20                  25                  30

Leu Glu Phe Leu Leu Asp Phe Cys Thr Gly Glu Asp Xaa Val Asp Gly
        35                  40                  45

Lys Lys Arg Gln Xaa His Xaa Xaa Xaa Xaa Xaa Xaa Xaa Xaa Xaa Ala
    50                  55                  60

Leu Pro Glu Pro Lys Ala Xaa
65                  70


<210> SEQ ID NO 14
<211> LENGTH: 74
<212> TYPE: PRT
<213> ORGANISM: BK polyomavirus

<400> SEQUENCE: 14

Met Phe Cys Glu Pro Lys Asn Leu Val Val Leu Arg Gln Leu Ser Arg
 1               5                  10                  15

Gln Ala Ser Val Lys Val Gly Lys Thr Trp Thr Gly Thr Lys Lys Arg
            20                  25                  30

Ala Gln Arg Ile Phe Ile Phe Ile Leu Glu Leu Leu Leu Glu Phe Cys
        35                  40                  45

Arg Gly Glu Asp Ser Val Asp Gly Lys Asn Lys Ser Thr Thr Ala Leu
    50                  55                  60

Pro Ala Val Lys Asp Ser Val Lys Asp Ser
65                  70


<210> SEQ ID NO 15
<211> LENGTH: 66
<212> TYPE: PRT
<213> ORGANISM: BK polyomavirus

<400> SEQUENCE: 15

Met Val Leu Arg Gln Leu Ser Arg Gln Ala Ser Val Lys Val Gly Lys
 1               5                  10                  15

Thr Trp Thr Gly Thr Lys Lys Arg Ala Gln Arg Ile Phe Ile Phe Ile
            20                  25                  30

Leu Glu Leu Leu Leu Glu Phe Cys Arg Gly Glu Asp Ser Val Asp Gly
        35                  40                  45

Lys Asn Lys Ser Thr Thr Ala Leu Pro Ala Val Lys Asp Ser Val Lys
    50                  55                  60

Asp Ser
65


<210> SEQ ID NO 16
<211> LENGTH: 21
<212> TYPE: PRT
<213> ORGANISM: BK polyomavirus

<400> SEQUENCE: 16

Met Val Leu Arg Gln Leu Ser Arg Gln Ala Ser Val Lys Leu Gly Lys
 1               5                  10                  15

Thr Trp Thr Gly Thr
            20


<210> SEQ ID NO 17
<211> LENGTH: 62
<212> TYPE: PRT
<213> ORGANISM: Simian virus 40

<400> SEQUENCE: 17
```

-continued

```
Met Val Leu Arg Arg Leu Ser Arg Gln Ala Ser Val Lys Val Arg Arg
 1               5                  10                  15

Ser Trp Thr Glu Ser Lys Lys Thr Ala Gln Arg Leu Phe Val Phe Val
            20                  25                  30

Leu Glu Leu Leu Leu Gln Phe Cys Glu Gly Glu Asp Thr Val Asp Gly
        35                  40                  45

Lys Arg Lys Lys Pro Glu Arg Leu Thr Glu Lys Pro Glu Ser
    50                  55                  60


<210> SEQ ID NO 18
<211> LENGTH: 225
<212> TYPE: DNA
<213> ORGANISM: BK polyomavirus

<400> SEQUENCE: 18

atgttttgcg agcctaagaa tcttgtggtt ttgcgccagc tgtcacgaca agcttcagtg      60

aaagttggta aaacctggac tggaactaaa aaaagagctc agaggatttt tatttttatt     120

ttagagcttt tgctggaatt ttgtagaggt gaagacagtg tagacgggaa aaacaaaagt     180

accactgctt tacctgctgt aaaagactct gtaaaagact cctag                     225


<210> SEQ ID NO 19
<211> LENGTH: 201
<212> TYPE: DNA
<213> ORGANISM: BK polyomavirus

<400> SEQUENCE: 19

atggttctgc gccagctgtc acgacaagct tcagtgaaag ttggtaaaac ctggactgga      60

acaaaaaaaa gagctcagag gatttttatt tttattttag agcttttgct ggaattttgt     120

agaggtgaag acagtgtaga cgggaaaaac aaaagtacca ctgctttacc tgctgtaaaa     180

gactctgtaa aagactccta g                                               201


<210> SEQ ID NO 20
<211> LENGTH: 63
<212> TYPE: DNA
<213> ORGANISM: BK polyomavirus

<400> SEQUENCE: 20

atggttctgc gccagctgtc acgacaagct tctgtgaaac ttggtaaaac ctggactgga      60

aca                                                                    63


<210> SEQ ID NO 21
<211> LENGTH: 189
<212> TYPE: DNA
<213> ORGANISM: Simian virus 40

<400> SEQUENCE: 21

atggtgctgc gccggctgtc acgccaggcc tccgttaagg ttcgtaggtc atggactgaa      60

agtaaaaaaa cagctcaacg cctttttgtg tttgttttag agcttttgct gcaattttgt     120

gaaggggaag atactgttga cgggaaacgc aaaaaaccag aaaggttaac tgaaaaacca     180

gaaagttaa                                                             189


<210> SEQ ID NO 22
<211> LENGTH: 64
<212> TYPE: PRT
<213> ORGANISM: JC virus
```

-continued

<400> SEQUENCE: 22

```
Met Val Leu Arg Gln Leu Ser Arg Lys Ala Ser Val Lys Val Ser Lys
 1               5                  10                  15

Thr Trp Ser Gly Thr Lys Lys Arg Ala Gln Arg Ile Leu Ile Phe Leu
            20                  25                  30

Leu Glu Phe Leu Leu Asp Phe Cys Thr Gly Glu Asp Ser Val Asp Gly
        35                  40                  45

Lys Lys Arg Gln Lys His Ser Gly Ala Leu Pro Glu Pro Lys Ala Thr
    50                  55                  60
```

<210> SEQ ID NO 23
<211> LENGTH: 195
<212> TYPE: DNA
<213> ORGANISM: JC virus

<400> SEQUENCE: 23

```
atggttcttc gccagctgtc acgtaaggct tctgtgaaag ttagtaaaac ctggagtgga      60

actaaaaaaa gagctcaaag gattttaatt tttttgttag aatttttgct ggatttttgc     120

acaggtgaag acagtgtaga cgggaaaaaa agacagaaac acagtggtgc tttgcctgaa     180

ccaaaagcta catag                                                      195
```

<210> SEQ ID NO 24
<211> LENGTH: 11
<212> TYPE: PRT
<213> ORGANISM: Artificial Sequence
<220> FEATURE:
<223> OTHER INFORMATION: Protein Transduction Domain

<400> SEQUENCE: 24

```
Tyr Gly Arg Lys Lys Arg Arg Gln Arg Arg Arg
 1               5                  10
```

<210> SEQ ID NO 25
<211> LENGTH: 34
<212> TYPE: DNA
<213> ORGANISM: Artificial Sequence
<220> FEATURE:
<223> OTHER INFORMATION: Primer

<400> SEQUENCE: 25

```
acgtccagga tccatggttc ttcgccagct gtca                                  34
```

<210> SEQ ID NO 26
<211> LENGTH: 34
<212> TYPE: DNA
<213> ORGANISM: Artificial Sequence
<220> FEATURE:
<223> OTHER INFORMATION: Primer

<400> SEQUENCE: 26

```
acgtccagaa ttcctatgta gcttttggtt cagg                                  34
```

<210> SEQ ID NO 27
<211> LENGTH: 30
<212> TYPE: DNA
<213> ORGANISM: Artificial Sequence -continued

```
<220> FEATURE:
<223> OTHER INFORMATION: Primer

<400> SEQUENCE: 27

tatgcggccg ctaatacgac tcactatagg                                   30


<210> SEQ ID NO 28
<211> LENGTH: 30
<212> TYPE: DNA
<213> ORGANISM: Artificial Sequence
<220> FEATURE:
<223> OTHER INFORMATION: Primer

<400> SEQUENCE: 28

tagaataggg ccctctagat gcatgctcga                                   30
```